US012343382B2

(12) United States Patent
Benson et al.

(10) Patent No.: US 12,343,382 B2
(45) Date of Patent: Jul. 1, 2025

(54) METHODS OF USING A GIP/GLP1 CO-AGONIST FOR THERAPY

(71) Applicant: Eli Lilly and Company, Indianapolis, IN (US)

(72) Inventors: Charles T. Benson, Zionsville, IN (US); Axel Haupt, Zionsville, IN (US); Melissa Kay Thomas, Indianapolis, IN (US); Shweta Urva, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 17/366,453

(22) Filed: Jul. 2, 2021

(65) Prior Publication Data

US 2021/0338781 A1 Nov. 4, 2021

Related U.S. Application Data

(62) Division of application No. 16/518,513, filed on Jul. 22, 2019, now abandoned.

(60) Provisional application No. 62/740,619, filed on Oct. 3, 2018, provisional application No. 62/730,565, filed on Sep. 13, 2018, provisional application No. 62/702,061, filed on Jul. 23, 2018.

(51) Int. Cl.
*A61K 38/26* (2006.01)

(52) U.S. Cl.
CPC .................... *A61K 38/26* (2013.01)

(58) Field of Classification Search
None
See application file for complete search history.

(56) References Cited

U.S. PATENT DOCUMENTS

| 9,474,780 B2 * | 10/2016 | Bokvist ........... A61K 38/16 |
| 10,278,923 B2 | 5/2019 | Nielsen et al. | |
| 11,357,820 B2 * | 6/2022 | Corvari ........... A61K 38/16 |

FOREIGN PATENT DOCUMENTS

| WO | 2013164483 | 11/2013 |
| WO | 2014177683 | 5/2014 |
| WO | 2015067715 | 5/2015 |
| WO | WO 2016/111971 | * 7/2016 |

OTHER PUBLICATIONS

Petri et al. (Diabetes Obes Metab. 2018;20:2238-2245) (Year: 2018).*
Coskun et al. (Mol Metab. Dec. 2018;18:3-14) (Year: 2018).*
University of Houston (downloaded on Mar. 27, 2023 from URL:< Associated growth chart.pdf (uh.edu)>) (Year: 2023).*
Clinical Trial NCT02759107 (May 3, 2016) (Year: 2016).*
"CDC" (download from URL:<https://www.cdc.gov/diabetes/about/about-type-1-diabetes.html>; 2024) (Year: 2024).*
"Cleveland Clinic" (downloaded from URL:<https://my.clevelandclinic.org/health/diseases/15831-fatty-liver-disease>; 2024) (Year: 2024).*
Taub, D. D. (1996). Chemokine-leukocyte interactions. The voodoo that they do so well. *Cytokine & growth factor reviews*, 7(4), 355-376.
Sun, F., et al. (2015). Gastrointestinal adverse events of glucagon-like peptide-1 receptor agonists in patients with type 2 diabetes: a systematic review and network meta-analysis. *Diabetes technology & therapeutics*, 17(1), 35-42.
Younossi, et al. (2016). Global epidemiology of nonalcoholic fatty liver disease—meta-analytic assessment of prevalence, incidence, and outcomes. *Hepatology*, 64(1), 73-84.
Portron, A., et al. (2017). Pharmacodynamics, pharmacokinetics, safety and tolerability of the novel dual glucose-dependent insulinotropic polypeptide/glucagon-like peptide-1 agonist RG 7697 after single subcutaneous administration in healthy subjects. *Diabetes, Obesity and Metabolism*, 19(10), 1446-1453.
Schmitt, C., et al. (2017). Pharmacodynamics, pharmacokinetics and safety of multiple ascending doses of the novel dual glucose-dependent insulinotropic polypeptide/glucagon-like peptide-1 agonist RG 7697 in people with type 2 diabetes mellitus. *Diabetes, Obesity and Metabolism*, 19(10), 1436-1445.
Wong, V. W. S., et al. (2018). Noninvasive biomarkers in NAFLD and NASH-current progress and future promise. *Nature Reviews Gastroenterology & Hepatology*, 15(8), 461 https://www.ncbi.nlm.nih.gov/pubmed/29844588.
Pratley, Richard, et. al. Oral semaglutide versus subcutaneous liraglutide and placebo in type 2 diabetes (PIONEER 4): a randomized, double blind, phase 3a tiral; The Lancet, (online Jun. 8, 2019).
International Search Report of the International Searching Authority pertaining to International Application No. PCT/US2019/042817; Date of Mailing: Jan. 9, 2020; 7 pages.
Written Opinion of the International Searching Authority pertaining to International Application No. PCT/US2019/042817; Date of Mailing: Jan. 9, 2020; 10 pages.
Chaplin, S., & Bain, S. (2016). Properties of GLP-1 agonists and their use in type 2 diabetes. *Prescriber*, 27(1), 43-46; 4 pages.

(Continued)

*Primary Examiner* — Sergio Coffa
(74) *Attorney, Agent, or Firm* — Parker D. McCrary; Matthew T. Lord; MaCharri R. Vorndran-Jones

(57) ABSTRACT

The present invention provides a method for increasing glycemic control in a patient in need thereof, by administering tirzepatide, or a pharmaceutically acceptable salt thereof. The present invention provides a method for improving weight management in a patient in need thereof, by administering tirzepatide, or a pharmaceutically acceptable salt thereof. Further providing a method for treating a condition selected from atherosclerosis, chronic kidney disease, NAFLD, and NASH. Further provided is a method to prevent or induce remission of diabetes comprising administration of tirzepatide, or a pharmaceutically acceptable salt thereof. Further provided is a dosing regimen for increasing glycemic control, improving weight management, and/or treating dyslipidemia.

51 Claims, No Drawings
Specification includes a Sequence Listing.

(56) References Cited

OTHER PUBLICATIONS

Will, S., Hornigold, D. C., Baker, D. J., Coghlan, M. P., Mesquita, M., Trevaskis, J. L., & Naylor, J. (2017). Gut check on diabesity: leveraging gut mechanisms for the treatment of type 2 diabetes and obesity. Current opinion in pharmacology. 37, 10-15; 6 pages.
Trial NCT02759107, A Study of LY3298176 in Healthy Participants and Participants With Type 2 Diabetes (T2DM), May 3, 2016 (Year: 2016).
Juan P. Frías et al., "Tirzepatide versus Semaglutide Once Weekly in Patients with Type 2 Diabetes," The New England Journal of Medicine, 385;6, Aug. 5, 2021, pp. 503-515.
Julio Rosenstock et al., "Achieving Normoglycemia With Tirzepatide: Analysis of SURPASS 1-4 Trials," Diabetes Care, vol. 46, Nov. 2023, pp. 1986-1992.
Closer Look, www.closerconcerns.com, EASD 2018 (European Association for the Study of Diabetes), Oct. 1-5, 2018; Berlin, Germany; Day #4 Highlights—Draft, pp. 1-29.
I8F-MC-GPGK(b) Clinical Protocol, "Protocol I8F-MC-GPGK(b) a Randomized, Double-blind, Placebo-Controlled Trial Comparing the Efficacy and Safety of Three Tirzepatide Does versus Placebo in Patients with Type 2 Diabetes, Inadequately Controlled with Diet and Exercise Alone (SURPASS-1)," Eli Lilly and Company, Indianapolis, Indiana USA 46285, Approval Date: Apr. 15, 2020 GMT, 91 pages.
I8F-MC-GPGL(b) Clinical Protocol, "Protocol I8F-MC-GPGL(b) a Phase 3, Randomized, Open-Label Trial Comparing Efficacy and Safety of Tirzepatide versus Semaglutide Once Weekly as Add-on Therapy to Metformin in Patients with Type 2 Diabetes (SURPASS-2)," Eli Lilly and Company, Indianapolis, Indiana USA 46285, Approval Date: Jun. 15, 2020 GMT, 99 pages.
I8F-MC-GPGH(c) Clinical Protocol, "Protocol I8F-MC-GPGH(c) a Randomized, Phase 3, Open-Label Trial Comparing the Effect of LY3298176 versus Titrated Insulin Degludec on Glycemic Control in Patients with Type 2 Diabetes (SURPASS-3)," Eli Lilly and Company, Indianapolis, Indiana USA 46285, Approval Date: Jul. 30, 2020 GMT, 95 pages.
I8F-MC-GPGM(b) Clinical Protocol, "Protocol I8F-MC-GPGM(b) Efficacy and Safety of LY3298176 Once Weekly versus Insulin Glargine in Patients with Type 2 Diabetes and Increased Cardiovascular Risk (SURPASS-4)," Eli Lilly and Company, Indianapolis, Indiana USA 46285, Approval Date: Jul. 10, 2020 GMT, 94 pages.
I8F-MC-GPGI(b) Clinical Protocol, "Protocol I8F-MC-GPGI(b) a Randomized, Phase 3, Double-blind Trial Comparing the Effect of the Addition of Tirzepatide versus Placebo in Patients with Type 2 Diabetes Inadequately Controlled on Insulin Glargine with or without Metformin (SURPASS-5)," Eli Lilly and Company, Indianapolis, Indiana USA 46285, Approval Date: Jun. 26, 2020 GMT, 100 pages.
Shizuka Kaneko, "Tirzepatide: A Novel, Once-weekly Dual GIP and GLP-1 Receptor Agonist for the Treatment of Type 2 Diabetes," Touch Medical Media, DOI: https://doi.org/10.17925/EE.2022.18.1.10, Jun. 16, 2022, pp. 10-19.
Tricia M-M Tan et al., "Tirzepatide and the new era of twincretins for diabetes," The Lancet, vol. 398, pp. 95-97, Jul. 10, 2021, Published Online Jun. 26, 2021, https://doi.org/10.1016/S0140-6736(21)01390-8.
Richard J. MacIsaac et al., Challenging Clinical Perspectives in Type 2 Diabetes with Tirzepatide, a First-in-Class Twincretin, Diabetes Ther (2023) 14:1997-2014, https://doi.org/10.1007/s13300-023-01475-5.
Alexis V. Fanshier et al., "Tirzepatide: A Novel Glucose-Dependent Insulinotropic Polypeptide/Glucagon-Like Peptide 1 Receptor Agonist for the Treatment of Type 2 Diabetes: The First Twincretin," Diabetes Journal, vol. 41, No. 3, pp. 367-377, Summer 2023.
Stefano Ciardullo et al., "GLP1-GIP receptor co-agonists: a promising evolution in the treatment of type 2 diabetes," Acta Diabetologica, https://doi.org/10.1007/s00592-024-02300-6, Published online: Jun. 3, 2024, 10 pages.
Julio Rosenstock et al., "Efficacy and safety of a novel dual GIP and GLP-1 receptor agonist tirzepatide in patients with type 2 diabetes (SURPASS-1): a double-blind, randomised, phase 3 trial," The Lancet, vol. 398, pp. 143-155, Jul. 10, 2021, Published Online Jun. 26, 2021.
Bernhard Ludvik et al., "Once-weekly tirzepatide versus once-daily insulin degludec as add-on to metformin with or without SGLT2 inhibitors in patients with type 2 diabetes (SURPASS-3): a randomised, open-label, parallel-group, phase 3 trial," The Lancet, vol. 398, pp. 583-598, Aug. 14, 2021, Published Online Aug. 6, 2021.
Stefano Del Prato et al., "Tirzepatide versus insulin glargine in type 2 diabetes and increased cardiovascular risk (SURPASS-4): a randomised, open-label, parallel-group, multicentre, phase 3 trial," The Lancet, vol. 398, pp. 1811-1824, Nov. 13, 2021, Published Online Oct. 18, 2021.
Michael A. Nauck et al., "Tirzepatide, a dual GIP/GLP-1 receptor co-agonist for the treatment of type 2 diabetes with unmatched effectiveness regrading glycaemic control and body weight reduction," Cardiovascular Diabetology, (2022), 21:169, 16 pages.
Closer Look, Practical Ways to Achieve Targets in Diabetes Care (Keystone) 2024, Jul. 10-13, 2024; Keystone, CO; Day #2 Highlights—Draft, www.closeconcerns.com, 18 pages.
Closer Look, American Diabetes Association 82nd Scientific Sessions, Jun. 3-7, 2022; New Orleans, LA (+Virtual); Day #2 Highlights—Draft, www.closeconcerns.com, 31 pages.
Diabetes_Core_Update_Nov_2023, diabetesjournals.org, 12 pages (transcript from audio podcast at diabetesjournals.org/journals/pages/diabetes-core-update-podcasts).
Closer Look, American Diabetes Association 82nd Scientific Sessions, Jun. 3-7, 2022; New Orleans, LA (+Virtual); Day #5 Highlights—Draft, www.closeconcerns.com, 37 pages.
Sunder Mudaliar, Diabetes remission—The holy grail in diabetes management, Chronicle of Diabetes Research and Practice, vol. 3, Issue 1, pp. 1-4, Jan.-Jun. 2024.
Djordje S. Popovic et al., "Achievement of normoglycemia with tirzepatide in type 2 diabetes mellitus: A step closer to drug-induced diabetes remission?," Journal of Diabetes and Its Complications 38 (2024) 108800, 3 pages.
Closer Look, ATTD (Advanced Technologies and Treatments for Diabetes) 2022, Apr. 27-30, 2022; Barcelona, Spain (+Virtual); Full Report—Draft, www.closeconcerns.com, 304 pages.

* cited by examiner

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is nonnaturally occurring
      amino acid 2-Aminoisobutyric Acid
<220> FEATURE:
<221> NAME/KEY: MISC_FEATURE
<222> LOCATION: (13)..(13)
<223> OTHER INFORMATION: Xaa at position 13 is nonnaturally occurring
      amino acid 2-Aminoisobutyric Acid
<220> FEATURE:
<221> NAME/KEY: MOD_RES
<222> LOCATION: (20)..(20)
<223> OTHER INFORMATION: Lys at position 20 is chemically modified
      through conjugation to the epsilon-amino group of the K side-chain
      with (2-[2-(2-Amino-ethoxy)-ethoxy]-acetyl)2-(gamma-Glu)1-CO-
      (CH2)18-CO2H
```

-continued

```
<220> FEATURE:
<221> NAME/KEY: MOD_RES
<222> LOCATION: (39)..(39)
<223> OTHER INFORMATION: Ser at position 39 is amidated as a C-terminal
      primary amide

<400> SEQUENCE: 1

Tyr Xaa Glu Gly Thr Phe Thr Ser Asp Tyr Ser Ile Xaa Leu Asp Lys
1               5                   10                  15

Ile Ala Gln Lys Ala Phe Val Gln Trp Leu Ile Ala Gly Gly Pro Ser
            20                  25                  30

Ser Gly Ala Pro Pro Pro Ser
            35
```

METHODS OF USING A GIP/GLP1 CO-AGONIST FOR THERAPY

This application is a divisional application of U.S. application Ser. No. 16/518,513, filed on Jul. 22, 2019, which claims priority to U.S. Provisional Application No. 62/740,619, filed on Oct. 3, 2018, to U.S. Provisional Application No. 62/730,565, filed on Sep. 13, 2018, and to U.S. Provisional Application No. 62/702,061, filed on Jul. 23, 2018. The disclosure of each of the above applications is incorporated herein by reference in its entirety.

REFERENCE TO AN ELECTRONIC SEQUENCE LISTING

The sequence listing is entitled "Sequence Listing" and is associated with the enclosed application, entitled "METHODS OF USING A GIP/GLP1 CO-AGONIST FOR THERAPY." The sequence listing was created on Jul. 22, 2019 and is 2 KB in size. The contents of the electronic sequence listing are herein incorporated by reference in their entirety.

The present invention provides methods of using novel doses of a glucose-dependent insulinotrophic polypeptide (GIP)/glucagon-like peptide-1 (GLP1) dual agonist peptide, tirzepatide, or a pharmaceutically acceptable salt thereof, to treat type 2 diabetes (T2D). Also, the present invention provides methods of using novel dosing regimens of a GIP/GLP1 dual agonist peptide, tirzepatide, or a pharmaceutically acceptable salt thereof, to treat type 2 diabetes. Furthermore, the present invention provides novel medical uses for tirzepatide, or a pharmaceutically acceptable salt thereof. More particularly, the present invention provides a method for treating a condition selected from the group of chronic kidney disease, atherosclerosis, nonalcoholic fatty liver disease ("NAFLD"), and nonalcoholic steatohepatitis ("NASH"). In a further embodiment, the present invention provides a method for curing diabetes in certain patients.

Diabetes mellitus is a chronic disorder characterized by hyperglycemia resulting from defects in insulin secretion, insulin action, or both. In T2D, the combined effects of impaired insulin secretion and insulin resistance are associated with elevated blood glucose levels.

U.S. Pat. No. 9,474,780 generally describes compositions containing a GIP/GLP1 co-agonist, administered by parenteral routes, and generally discloses a wide dosage range up to about 30 mg per person per week. U.S. Pat. No. 9,474,780 discloses the use of GIP/GLP1 co-agonists for treating diabetes, obesity, and other conditions. U.S. Pat. No. 9,474,780 describes and claims tirzepatide.

It is well-known that GLP1 treatments are associated with nausea, vomiting, and/or diarrhea. For example, one study reported that all GLP-1 receptor agonist dosing regimens significantly increased the incidence of gastrointestinal adverse events. *Diabetes Technol Ther.* 2015 January; 17(1): 35-42. Also, previous clinical trials of a GIP/GLP1 co-agonist compound have been performed and found that tolerability at high doses was limited by gastrointestinal adverse events. Schmitt, C. et al. "Pharmacodynamics, pharmacokinetics and safety of multiple ascending doses of the novel dual glucose-dependent insulinotrophic polypeptide/glucagon-like peptide-1 agonist RG7697 in people with type 2 diabetes mellitus." *Diabetes Obes. Metab.* 2017; 19:1436-1445. Portron, A. et al. "Pharmacodynamics, Pharmacokinetics, Safety, and Tolerability of the Novel Dual GIP/GLP-1 Agonist (RG7697) after Single Subcutaneous Administration in Healthy Subjects." 2390-PUB, A624, ADA-2017; Portron, A. et al. "Pharmacodynamics, pharmacokinetics, safety and tolerability of the novel dual glucose-dependent insulinotrophic polypeptide/glucagon-like peptide-1 agonist RG7697 after single subcutaneous administration in healthy subjects." *Diabetes Obes. Metab.* 2017; 19:14446-1453. The dose limitation associated with gastrointestinal adverse events may prevent dosing to the desired effective dose, may compromise patient compliance with treatment, and may limit the effectiveness of the treatment regimen.

There is a need for novel doses of tirzepatide to provide desired glycemic control, as evidenced for example, by further reductions of HbA1c, and/or weight loss, while maintaining an acceptable profile of safety and adverse events. There is also a need for a novel dosing regimen of tirzepatide to provide desired glycemic control, as evidenced for example, by further reductions of HbA1c, and/or weight loss, while maintaining an acceptable profile of safety and adverse events. Also, there is a need for a GIP/GLP1 dual agonist treatment option for a condition selected from chronic kidney disease, atherosclerosis, NAFLD, and NASH. Furthermore, there is a desire for a treatment to cure diabetes by preventing, reducing severity of, or inducing remission of diabetes. There is a desire for a treatment to reduce or delay progression of diabetes.

The present invention provides novel tirzepatide dosing regimens for use in the aforementioned therapies that include a maintenance dose selected from the group consisting of: about 5.0 mg, about 10.0 mg and about 15.0 mg. In another embodiment, the present invention provides novel dosing regimens that include an escalation dose (i.e., a dose lower than the desired maintenance dose) and a maintenance dose. In another embodiment, the present invention provides novel dosing regimens that include one or more escalation doses and one or more maintenance doses. The present invention provides novel dosing regimens that include administering at least one escalation dose about once weekly for a minimum of about four weeks and thereafter at least one maintenance dose about once weekly for a minimum of about four weeks. In certain embodiment, the doses may be administered for about four weeks. In certain embodiments, the doses may be administered for more than about four weeks as determined by the nurse, patient and/or health care provider. For example, a maintenance dose may be administered for more than about four weeks. In certain embodiments of the present invention a maintenance dose may be increased to the next highest maintenance dose of the present invention if additional glycemic control is needed with or without an intervening escalation dose. For example, in one dosing regimen according to the present invention, the escalation dose is about 2.5 mg and the maintenance dose is about 5.0 mg. In another dosing regimen according to the present invention, two escalation doses are about 2.5 mg and about 7.5 mg and the maintenance doses are about 5.0 mg and 10.0 mg. In another aspect of the present invention, the escalation doses are about 2.5 mg, about 7.5 mg and about 12.5 mg and the maintenance doses are about 5.0 mg, about 10.0 mg and about 15.0 mg. Escalation doses include about 2.5 mg, about 7.5 mg and about 12.5 mg. Maintenance doses include about 5.0 mg, about 10.0 mg and about 15.0 mg. An escalation dose of 2.5 mg may be the initial dose, or starting dose, for the dosing regimen provided herein. As used herein, the term "escalation" or "escalation dose(s)" means a titration or titration dose, as described herein.

Accordingly, the present invention provides a method of treating type 2 diabetes in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose. An embodiment of the present invention is thus a method of treating type 2 diabetes wherein the escalation dose administered about once weekly for at least about four weeks is about 2.5 mg and the maintenance dose administered about once weekly for at least about four weeks is about 5.0 mg. A further embodiment of the present invention is a method wherein the escalation dose administered about once weekly for at least about four weeks is about 7.5 mg and the maintenance dose administered about once weekly for at least about four weeks is about 10.0 mg. A further embodiment of the present invention is a method wherein the escalation dose administered about once weekly for at least about four weeks is about 12.5 mg and the maintenance dose administered about once weekly for at least about four weeks is about 15.0 mg. A further embodiment of the present invention is wherein after a first maintenance dose has been administered for the at least about four weeks, a second escalation dose is administered about once weekly for at least about four weeks and thereafter a second maintenance dose is administered about once weekly for at least about four weeks. One such method thus includes escalation doses of about 2.5 mg and about 7.5 mg and maintenance doses of about 5.0 mg and about 10.0 mg. Another embodiment of the present invention is one where after a second maintenance does has been administered for the at least about four weeks, a third escalation dose is administered about once weekly for at least about four weeks and thereafter a third maintenance does is administered about once weekly for at least about four weeks. One such method thus includes escalation doses of about 2.5 mg, about 7.5 mg and about 12.5 mg and maintenance doses of about 5.0 mg, about 10.0 mg and about 15.0 mg.

As noted above, in certain embodiments of the present invention a maintenance dose may be increased to a subsequent maintenance dose if additional glycemic control is needed with or without an intervening escalation dose. Thus, the present invention further provides a method of treating type 2 diabetes in a patient in need thereof, comprising: administering an escalation dose of about 2.5 mg of tirzepatide, or a pharmaceutically acceptable salt thereof, about once weekly for a minimum of about four weeks and thereafter administering a maintenance dose of about 5.0 mg of tirzepatide, or a pharmaceutically acceptable salt thereof, about once weekly for a minimum of about four weeks; and, optionally thereafter, administering a second maintenance dose of about 10.0 mg of tirzepatide, or a pharmaceutically acceptable salt thereof, about once weekly for a minimum of about four weeks; and, optionally thereafter, administering a third maintenance dose of about 15.0 mg of tirzepatide, or a pharmaceutically acceptable salt thereof, about once weekly for a minimum of about four weeks.

In another aspect the present invention provides a method of treating type 2 diabetes in a patient in need thereof, comprising:

a) administering to said patient a dose of about 2.5 mg of tirzepatide, or a pharmaceutically acceptable salt thereof, about once weekly for a minimum of about four weeks;
b) increasing the dose to a dose of about 5.0 mg of tirzepatide, or a pharmaceutically acceptable salt thereof, and administering to said patient about once weekly for a minimum of about four weeks;
c) increasing the dose to a dose of about 7.5 mg of tirzepatide, or a pharmaceutically acceptable salt thereof, and administering to said patient about once weekly for a minimum of about four weeks;
d) increasing the dose to a dose of about 10.0 mg of tirzepatide, or a pharmaceutically acceptable salt thereof, and administering to said patient about once weekly for a minimum of about four weeks;
e) increasing the dose to a dose of about 12.5 mg of tirzepatide, or a pharmaceutically acceptable salt thereof, and administering to said patient about once weekly for a minimum of about four weeks; and
f) increasing the dose to a dose of about 15.0 mg of tirzepatide, or a pharmaceutically acceptable salt thereof, and administering to said patient about once weekly for a minimum of about four weeks.

In one aspect, the present invention provides a method of treating type 2 diabetes in a patient in need thereof, comprising:

a) administering to said patient an escalation dose of about 2.5 mg of tirzepatide, or a pharmaceutically acceptable salt thereof, about once weekly for a minimum of about four weeks; and thereafter
b) administering to said patient a maintenance dose of about 5.0 mg of tirzepatide, or a pharmaceutically acceptable salt thereof, about once weekly for a minimum of about four weeks.

In another aspect, the present invention provides a method of treating type 2 diabetes in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a method of treating type 2 diabetes in a patient in need thereof, comprising:

a) administering to said patient a maintenance dose of about 5.0 mg of tirzepatide, or a pharmaceutically acceptable salt thereof, about once weekly for a minimum of about four weeks; and thereafter
b) administering to said patient a maintenance dose of about 10.0 mg of tirzepatide, or a pharmaceutically acceptable salt thereof, about once weekly for a minimum of about four weeks.

Another embodiment provides a method of treating type 2 diabetes in a patient in need thereof, comprising:

a) administering to said patient an escalation dose of about 7.5 mg of tirzepatide, or a pharmaceutically acceptable salt thereof, about once weekly for a minimum of about four weeks; and thereafter
b) administering to said patient a maintenance dose of about 10.0 mg of tirzepatide, or a pharmaceutically acceptable salt thereof, about once weekly for a minimum of about four weeks.

In another aspect, the present invention provides a method of treating type 2 diabetes in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a method of treating type 2 diabetes in a patient in need thereof, comprising:
a) administering to said patient a maintenance dose of about 10.0 mg of tirzepatide, or a pharmaceutically acceptable salt thereof, about once weekly for a minimum of about four weeks; and thereafter
b) administering to said patient a maintenance dose of about 15.0 mg of tirzepatide, or a pharmaceutically acceptable salt thereof, about once weekly for a minimum of about four weeks.

Another embodiment provides a method of treating type 2 diabetes in a patient in need thereof, comprising:
a) administering to said patient an escalation dose of about 12.5 mg of tirzepatide, or a pharmaceutically acceptable salt thereof, about once weekly for a minimum of about four weeks; and thereafter
b) administering to said patient a maintenance dose of about 15.0 mg of tirzepatide, or a pharmaceutically acceptable salt thereof, about once weekly for a minimum of about four weeks.

In another aspect, the present invention provides a method treating type 2 diabetes in a patient in need thereof, comprising: administering to said patient a maintenance dose of about 15.0 mg of tirzepatide, or a pharmaceutically acceptable salt thereof, about once weekly for a minimum of about four weeks.

In another aspect, the present invention provides a method of treating type 2 diabetes in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient a maintenance dose of about 5.0 mg of tirzepatide, or a pharmaceutically acceptable salt thereof, about once weekly for a minimum of about four weeks; and thereafter
c) administering to said patient an escalation dose of about 7.5 mg of tirzepatide, or a pharmaceutically acceptable salt thereof, about once weekly for a minimum of about four weeks; and thereafter
d) administering to said patient a maintenance dose of about 10.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose.

In another aspect, the present invention provides a method of treating type 2 diabetes in a patient in need thereof, comprising:
g) administering to said patient an escalation dose of about 2.5 mg of tirzepatide, or a pharmaceutically acceptable salt thereof, about once weekly for a minimum of about four weeks; and thereafter
h) administering to said patient a maintenance dose of about 5.0 mg of tirzepatide, or a pharmaceutically acceptable salt thereof, about once weekly for a minimum of about four weeks; and thereafter
i) administering to said patient an escalation dose of about 7.5 mg of tirzepatide, or a pharmaceutically acceptable salt thereof, about once weekly for a minimum of about four weeks; and thereafter
j) administering to said patient a maintenance dose of about 10.0 mg of tirzepatide, or a pharmaceutically acceptable salt thereof, about once weekly for a minimum of about four weeks; and thereafter
k) administering to said patient an escalation dose of about 12.5 mg of tirzepatide, or a pharmaceutically acceptable salt thereof, about once weekly for a minimum of about four weeks; and thereafter
l) administering to said patient a maintenance dose of about 15.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose. In another aspect, the present invention includes a method as described in the preceding paragraph but which does not include administering the 12.5 mg escalation dose. In another aspect, the present invention includes a method as described in the preceding paragraph but which does not include administering the 7.5 mg and 12.5 mg escalation doses.

Furthermore, the present invention provides a method of improving glycemic control in a patient in need thereof, comprising: administering at least one escalation dose about once weekly for a minimum of about four weeks and at least one maintenance dose about once weekly for a minimum of about four weeks following the escalation dose; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose. An embodiment of the present invention is thus a method of improving glycemic control wherein the escalation dose administered about once weekly for at least about four weeks is about 2.5 mg and the maintenance dose administered about once weekly for at least about four weeks is about 5.0 mg. A further embodiment of the present invention is a method wherein the escalation dose administered about once weekly for at least about four weeks is about 7.5 mg and the maintenance dose administered about once weekly for at least about four weeks is about 10.0 mg. A further embodiment of the present invention is a method wherein the escalation dose administered about once weekly for at least about four weeks is about 12.5 mg and the maintenance dose administered about once weekly for at least about four weeks is about 15.0 mg. A further embodiment of the present invention is wherein after a first maintenance dose has been administered for the at least about four weeks, a second escalation dose is administered about once weekly for at least about four weeks and thereafter a second maintenance dose is administered about once weekly for at least about four weeks. One such method thus includes escalation doses of about 2.5 mg and about 7.5 mg and maintenance doses of about 5.0 mg and about 10.0 mg. A further embodiment of the present invention is one where after a second maintenance dose has been administered for the at least about four weeks, a third escalation dose is administered about once weekly for at least about four weeks and thereafter a third maintenance does is administered about once weekly for at least about four weeks. One such method thus includes escalation doses of about 2.5 mg, about 7.5 mg and about 12.5 mg and maintenance doses of about 5.0 mg, about 10.0 mg and about 15.0 mg.

As noted above, in certain embodiments of the present invention a maintenance dose may be increased to a subsequent maintenance dose if additional glycemic control is needed with or without an intervening escalation dose. Thus, the present invention further provides a method of improving glycemic control in a patient in need thereof, comprising: administering an escalation dose of about 2.5 mg of tirzepatide, or a pharmaceutically acceptable salt thereof, about once weekly for a minimum of about four weeks and thereafter administering a maintenance dose of about 5.0 mg of tirzepatide, or a pharmaceutically acceptable salt thereof, about once weekly for a minimum of about four weeks; and, optionally thereafter, administering a second maintenance dose of about 10.0 mg of tirzepatide, or a pharmaceutically acceptable salt thereof, about once weekly for a minimum of about four weeks; and, optionally thereafter, administering a third maintenance dose of about 15.0 mg of tirzepatide, or a pharmaceutically acceptable salt thereof, about once weekly for a minimum of about four weeks.

Furthermore, the present invention provides a method of improving glycemic control in a patient in need thereof, comprising:
  a) administering to said patient an escalation dose of about 2.5 mg of tirzepatide, or a pharmaceutically acceptable salt thereof, about once weekly for a minimum of about four weeks; and thereafter
  b) administering to said patient a maintenance dose of about 5.0 mg of tirzepatide, or a pharmaceutically acceptable salt thereof, about once weekly for a minimum of about four weeks.

In another aspect the present invention provides a method of improving glycemic control in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a method of improving glycemic control in a patient in need thereof comprising:
  a) administering to said patient a maintenance dose of about 5.0 mg of tirzepatide, or a pharmaceutically acceptable salt thereof, about once weekly for a minimum of about four weeks; and thereafter
  b) administering to said patient a maintenance dose of about 10.0 mg of tirzepatide, or a pharmaceutically acceptable salt thereof, about once weekly for a minimum of about four weeks.

Another embodiment provides a method of improving glycemic control in a patient in need thereof comprising:
  a) administering to said patient an escalation dose of about 7.5 mg of tirzepatide, or a pharmaceutically acceptable salt thereof, about once weekly for a minimum of about four weeks; and thereafter
  b) administering to said patient a maintenance dose of about 10.0 mg of tirzepatide, or a pharmaceutically acceptable salt thereof, about once weekly for a minimum of about four weeks.

In another aspect the present invention provides a method of improving glycemic control in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a method of improving glycemic control in a patient in need thereof comprising:
  a) administering to said patient a maintenance dose of about 10.0 mg of tirzepatide, or a pharmaceutically acceptable salt thereof, about once weekly for a minimum of about four weeks; and thereafter
  b) administering to said patient a maintenance dose of about 15.0 mg of tirzepatide, or a pharmaceutically acceptable salt thereof, about once weekly for a minimum of about four weeks.

Another embodiment provides a method of improving glycemic control in a patient in need thereof, comprising:
  a) administering to said patient an escalation dose of about 12.5 mg of tirzepatide, or a pharmaceutically acceptable salt thereof, about once weekly for a minimum of about four weeks; and thereafter
  b) administering to said patient a maintenance dose of about 15.0 mg of tirzepatide, or a pharmaceutically acceptable salt thereof, about once weekly for a minimum of about four weeks.

In another aspect the present invention provides a method of improving glycemic control in a patient in need thereof, comprising: administering to said patient a maintenance dose of about 15.0 mg of tirzepatide, or a pharmaceutically acceptable salt thereof, about once weekly for a minimum of about four weeks.

In another aspect the present invention provides a method of improving glycemic control in a patient in need thereof, comprising:
  a) administering to said patient an escalation dose of about 2.5 mg of tirzepatide, or a pharmaceutically acceptable salt thereof, about once weekly for a minimum of about four weeks; and thereafter
  b) administering to said patient a maintenance dose of about 5.0 mg of tirzepatide, or a pharmaceutically acceptable salt thereof, about once weekly for a minimum of about four weeks; and thereafter
  c) administering to said patient an escalation dose of about 7.5 mg of tirzepatide, or a pharmaceutically acceptable salt thereof, about once weekly for a minimum of about four weeks; and thereafter
  d) administering to said patient a maintenance dose of about 10.0 mg of tirzepatide, or a pharmaceutically acceptable salt thereof, about once weekly for a minimum of about four weeks; and thereafter In another aspect, the present invention includes a method as described in the preceding paragraph but which does not include administering the 7.5 mg escalation dose.

In another aspect, the present invention provides a method of improving glycemic control in a patient in need thereof, comprising:
  a) administering to said patient an escalation dose of about 2.5 mg of tirzepatide, or a pharmaceutically acceptable salt thereof, about once weekly for a minimum of about four weeks; and thereafter
  b) administering to said patient a maintenance dose of about 5.0 mg of tirzepatide, or a pharmaceutically acceptable salt thereof, about once weekly for a minimum of about four weeks; and thereafter
  c) administering to said patient an escalation dose of about 7.5 mg of tirzepatide, or a pharmaceutically acceptable salt thereof, about once weekly for a minimum of about four weeks; and thereafter
  d) administering to said patient a maintenance dose of about 10.0 mg of tirzepatide, or a pharmaceutically acceptable salt thereof, about once weekly for a minimum of about four weeks; and thereafter
  e) administering to said patient an escalation dose of about 12.5 mg of tirzepatide, or a pharmaceutically acceptable salt thereof, about once weekly for a minimum of about four weeks; and thereafter f) administering to said patient a maintenance dose of about 15.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose. In another aspect, the present invention includes a method as described in the preceding paragraph but which does not include administering the 12.5 mg escalation dose. In another aspect, the present invention includes a method as described in the preceding paragraph but which does not include administering the 7.5 mg and 12.5 mg escalation doses.

In a further embodiment, is a method for treating type 2 diabetes in a patient in need thereof, comprising: administering tirzepatide, or a pharmaceutically acceptable salt thereof, in a tirzepatide dosing regimen that comprises an initiation phase, at least one escalation phase, and a maintenance phase; wherein the initiation phase comprises administration of 2.5 mg tirzepatide, or a pharmaceutically acceptable salt thereof, about once weekly for at least about 2 to 4 weeks; wherein the escalation phase comprises administration of a dose that is increased from the initiation phase dose or prior escalation phase dose by about 2.5 mg per week for at least about 2 to 4 weeks per escalation phase, wherein the escalation dose increases by 2.5 mg during each escalation phase until the maintenance phase is reached; and wherein the maintenance phase is about once weekly administration of a dose selected from the group consisting of about 5 mg, about 10 mg and about 15 mg tirzepatide, or a pharmaceutically acceptable salt thereof.

Also, the present invention provides a method of improving weight management in a patient in need thereof, comprising: administering an escalation dose about once weekly for a minimum of about four weeks and thereafter administering at least one maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose. An embodiment of the present invention is thus a method of improving weight management wherein the escalation dose administered about once weekly for at least about four weeks is about 2.5 mg and the maintenance dose administered about once weekly for at least about four weeks is about 5.0 mg. A further embodiment of the present invention is a method wherein the escalation dose administered about once weekly for at least about four weeks is about 7.5 mg and the maintenance dose administered about once weekly for at least about four weeks is about 10.0 mg. A further embodiment of the present invention is a method wherein the escalation dose administered about once weekly for at least about four weeks is about 12.5 mg and the maintenance dose administered about once weekly for at least about four weeks is about 15.0 mg. A further embodiment of the present invention is wherein after a first maintenance dose has been administered for the at least about four weeks, a second escalation dose is administered about once weekly for at least about four weeks and thereafter a second maintenance dose is administered about once weekly for at least about four weeks. One such method thus includes escalation doses of about 2.5 mg and about 7.5 mg and maintenance doses of about 5.0 mg and about 10.0 mg. Another embodiment of the present invention is one where after a second maintenance does has been administered for the at least about four weeks, a third escalation dose is administered about once weekly for at least about four weeks and thereafter a third maintenance does is administered about once weekly for at least about four weeks. One such method thus includes escalation doses of about 2.5 mg, about 7.5 mg and about 12.5 mg and maintenance doses of about 5.0 mg, about 10.0 mg and about 15.0 mg.

As noted above, in certain embodiments of the present invention a maintenance dose may be increased to a subsequent maintenance dose if additional glycemic control is needed with or without an intervening escalation dose. Thus, the present invention further provides a method of improving weight management in a patient in need thereof, comprising: administering an escalation dose of about 2.5 mg of tirzepatide, or a pharmaceutically acceptable salt thereof, about once weekly for a minimum of about four weeks and thereafter administering a maintenance dose of about 5.0 mg of tirzepatide, or a pharmaceutically acceptable salt thereof, about once weekly for a minimum of about four weeks; and, optionally thereafter, administering a second maintenance dose of about 10.0 mg of tirzepatide, or a pharmaceutically acceptable salt thereof, about once weekly for a minimum of about four weeks; and, optionally thereafter, administering a third maintenance dose of about 15.0 mg of tirzepatide, or a pharmaceutically acceptable salt thereof, about once weekly for a minimum of about four weeks.

In yet another aspect, the present invention provides a method of improving weight management in a patient in need thereof comprising:
 a) administering to said patient an escalation dose of about 2.5 mg of tirzepatide, or a pharmaceutically acceptable salt thereof, about once weekly for a minimum of about four weeks; and thereafter
 b) administering to said patient a maintenance dose of about 5.0 mg of tirzepatide, or a pharmaceutically acceptable salt thereof, about once weekly for a minimum of about four weeks.

In another aspect, the present invention provides a method of improving weight management in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a method of improving weight management in a patient in need thereof, comprising:
 a) administering to said patient a maintenance dose of about 5.0 mg of tirzepatide, or a pharmaceutically acceptable salt thereof, about once weekly for a minimum of about four weeks; and thereafter
 b) administering to said patient a maintenance dose of about 10.0 mg of tirzepatide, or a pharmaceutically acceptable salt thereof, about once weekly for a minimum of about four weeks.

Another embodiment provides a method of improving weight management in a patient in need thereof, comprising:
 a) administering to said patient an escalation dose of about 7.5 mg of tirzepatide, or a pharmaceutically acceptable salt thereof, about once weekly for a minimum of about four weeks; and thereafter
 b) administering to said patient a maintenance dose of about 10.0 mg of tirzepatide, or a pharmaceutically acceptable salt thereof, about once weekly for a minimum of about four weeks.

In another aspect, the present invention provides a method of improving weight management in a patient in need thereof comprising: administering to said patient a maintenance dose of about 10.0 mg of tirzepatide, or a pharmaceutically acceptable salt thereof, about once weekly for a minimum of about four weeks.

Another embodiment provides a method of improving weight management in a patient in need thereof, comprising:
a) administering to said patient a maintenance dose of about 10.0 mg of tirzepatide, or a pharmaceutically acceptable salt thereof, about once weekly for a minimum of about four weeks; and thereafter
b) administering to said patient a maintenance dose of about 15.0 mg of tirzepatide, or a pharmaceutically acceptable salt thereof, about once weekly for a minimum of about four weeks.

Another embodiment provides a method of improving weight management in a patient in need thereof, comprising:
a) administering to said patient an escalation dose of about 12.5 mg of tirzepatide, or a pharmaceutically acceptable salt thereof, about once weekly for a minimum of about four weeks; and
b) administering to said patient a maintenance dose of about 15.0 mg of tirzepatide, or a pharmaceutically acceptable salt thereof, about once weekly for a minimum of about four weeks.

In another aspect, the present invention provides a method of improving weight management in a patient in need thereof, comprising: administering to said patient a maintenance dose of about 15.0 mg of tirzepatide, or a pharmaceutically acceptable salt thereof, about once weekly for a minimum of about four weeks.

In another aspect, the present invention provides a method of improving weight management in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient a maintenance dose of about 5.0 mg of tirzepatide, or a pharmaceutically acceptable salt thereof, about once weekly for a minimum of about four weeks; and thereafter
c) administering to said patient an escalation dose of about 7.5 mg of tirzepatide, or a pharmaceutically acceptable salt thereof, about once weekly for a minimum of about four weeks; and thereafter
d) administering to said patient a maintenance dose of about 10.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose.

In another aspect, the present invention provides a method of improving weight management in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient a maintenance dose of about 5.0 mg of tirzepatide, or a pharmaceutically acceptable salt thereof, about once weekly for a minimum of about four weeks; and thereafter
c) administering to said patient an escalation dose of about 7.5 mg of tirzepatide, or a pharmaceutically acceptable salt thereof, about once weekly for a minimum of about four weeks; and thereafter
d) administering to said patient a maintenance dose of about 10.0 mg of tirzepatide, or a pharmaceutically acceptable salt thereof, about once weekly for a minimum of about four weeks; and thereafter
e) administering to said patient an escalation dose of about 12.5 mg of tirzepatide, or a pharmaceutically acceptable salt thereof, about once weekly for a minimum of about four weeks; and thereafter
f) administering to said patient a maintenance dose of about 15.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose. In another aspect, the present invention includes a method as described in the preceding paragraph but which does not include administering the 12.5 mg escalation dose. In another aspect, the present invention includes a method as described in the preceding paragraph but which does not include administering the 7.5 mg and 12.5 mg escalation doses.

Also, the present invention provides a method of treating chronic kidney disease in a patient in need thereof, comprising: administering am escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof: wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose. An embodiment of the present invention for a method of treating chronic kidney disease wherein the escalation dose administered about once weekly for at least about four weeks is about 2.5 mg and the maintenance dose administered about once weekly for at least about four weeks is about 5.0 mg. A further embodiment of the present invention is a method wherein the escalation dose administered about once weekly for at least about four weeks is about 7.5 mg and the maintenance dose administered about once weekly for at least about four weeks is about 10.0 mg. A further embodiment of the present invention is a method wherein the escalation dose administered about once weekly for at least about four weeks is about 12.5 mg and the maintenance dose administered about once weekly for at least about four weeks is about 15.0 mg. A further embodiment of the present invention is wherein the escalation doses administered about once weekly for at least about four weeks are about 2.5 mg and about 7.5 mg and the maintenance doses administered about once weekly for at least about four weeks are about 5.0 mg and about 10.0 mg. A further embodiment of the present invention is wherein the escalation doses administered about once weekly for at least about four weeks are about 2.5 mg, about 5.0 mg and about 7.5 mg and the maintenance doses administered about once weekly for at least about four weeks are about 5.0 mg, about 10.0 mg and about 15.0 mg.

Accordingly, the present invention provides a method of treating chronic kidney disease in a patient in need thereof, comprising:
a) administering to said patient an escalation dose of about 2.5 mg of tirzepatide, or a pharmaceutically acceptable salt thereof, about once weekly for a minimum of about four weeks; and thereafter b) administering to said patient about 5.0 mg of tirzepatide, or a pharmaceutically acceptable salt thereof, about once weekly for a minimum of about four weeks.

In another aspect, the present invention provides a method of treating chronic kidney disease in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a method of treating chronic kidney disease in a patient in need thereof comprising:

a) administering to said patient a maintenance dose of about 5.0 mg of tirzepatide, or a pharmaceutically acceptable salt thereof, about once weekly for a minimum of about four weeks; and thereafter b) administering to said patient about 10.0 mg of tirzepatide, or a pharmaceutically acceptable salt thereof, about once weekly for a minimum of about four weeks.

Another embodiment provides a method of treating chronic kidney disease in a patient in need thereof comprising:

a) administering to said patient an escalation dose of about 7.5 mg of tirzepatide, or a pharmaceutically acceptable salt thereof, about once weekly for a minimum of about four weeks; and thereafter b) administering to said patient about 10.0 mg of tirzepatide, or a pharmaceutically acceptable salt thereof, about once weekly for a minimum of about four weeks.

In another aspect, the present invention provides a method of treating chronic kidney disease in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a method of treating chronic kidney disease in a patient in need thereof comprising:

a) administering to said patient a maintenance dose of about 10.0 mg of tirzepatide, or a pharmaceutically acceptable salt thereof, about once weekly for a minimum of about four weeks; and thereafter b) administering to said patient about 15.0 mg of tirzepatide, or a pharmaceutically acceptable salt thereof, about once weekly for a minimum of about four weeks.

Another embodiment provides a method of treating chronic kidney disease in a patient in need thereof, comprising:

a) administering to said patient an escalation dose of about 12.5 mg of tirzepatide, or a pharmaceutically acceptable salt thereof, about once weekly for a minimum of about four weeks; and thereafter b) administering to said patient about 15.0 mg of tirzepatide, or a pharmaceutically acceptable salt thereof, about once weekly for a minimum of about four weeks.

In another aspect, the present invention provides a method of treating chronic kidney disease in a patient in need thereof comprising: administering to said patient a maintenance dose of about 15.0 mg of tirzepatide, or a pharmaceutically acceptable salt thereof, about once weekly for a minimum of about four weeks.

In another aspect, the present invention provides a method of treating chronic kidney disease in a patient in need thereof, comprising:

a) administering to said patient an escalation dose of about 2.5 mg of tirzepatide, or a pharmaceutically acceptable salt thereof, about once weekly for a minimum of about four weeks; and thereafter b) administering to said patient a maintenance dose of about 5.0 mg of tirzepatide, or a pharmaceutically acceptable salt thereof, about once weekly for a minimum of about four weeks; and thereafter c) administering to said patient an escalation dose of about 7.5 mg of tirzepatide, or a pharmaceutically acceptable salt thereof, about once weekly for a minimum of about four weeks; and thereafter d) administering to said patient a maintenance dose of about 10.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose.

In another aspect, the present invention provides a method of treating chronic kidney disease in a patient in need thereof, comprising:

a) administering to said patient an escalation dose of about 2.5 mg of tirzepatide, or a pharmaceutically acceptable salt thereof, about once weekly for a minimum of about four weeks; and thereafter b) administering to said patient a maintenance dose of about 5.0 mg of tirzepatide, or a pharmaceutically acceptable salt thereof, about once weekly for a minimum of about four weeks; and thereafter c) administering to said patient an escalation dose of about 7.5 mg of tirzepatide, or a pharmaceutically acceptable salt thereof, about once weekly for a minimum of about four weeks; and thereafter d) administering to said patient a maintenance dose of about 10.0 mg of tirzepatide, or a pharmaceutically acceptable salt thereof, about once weekly for a minimum of about four weeks; and thereafter e) administering to said patient an escalation dose of about 12.5 mg of tirzepatide, or a pharmaceutically acceptable salt thereof, about once weekly for a minimum of about four weeks; and thereafter f) administering to said patient a maintenance dose of about 15.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose. In another aspect, the present invention includes a method as described in the preceding paragraph but which does not include administering the 12.5 mg escalation dose. In another aspect, the present invention includes a method as described in the preceding paragraph but which does not include administering the 7.5 mg and 12.5 mg escalation doses.

In a further embodiment, is a method for treating diabetic kidney disease, in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose.

Also, the present invention provides a method of treating atherosclerosis in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof, and wherein the maintenance dose following an escalation dose is a 2.5 mg incremental increase relative to that escalation dose. An embodiment of the present invention for a method of treating atherosclerosis wherein the escalation dose administered about once weekly for at least about four weeks is about 2.5 mg and the maintenance dose administered about once weekly for at least about four weeks is about 5.0 mg. A further embodiment of the present invention is a method wherein the escalation dose administered about once weekly for at least about four weeks is about 7.5 mg and the maintenance dose administered about once weekly for at least about four weeks is about 10.0 mg. A further embodiment of the present invention is a method wherein the escalation dose administered about once weekly for at least about four weeks is about 12.5 mg and the maintenance dose administered about once weekly for at least about four weeks is about 15.0 mg. A further embodiment of the present invention is wherein the escalation doses administered about once weekly for at least about four weeks are about 2.5 mg and about 7.5 mg and the maintenance doses administered about once weekly for at least about four weeks are about 5.0 mg and about 10.0 mg. A further embodiment of the present invention is wherein the escalation doses administered about once weekly for at least about four weeks are about 2.5 mg, about 5.0 mg and about 7.5 mg and the maintenance doses administered about once weekly for at least about four weeks are about 5.0 mg, about 10.0 mg and about 15.0 mg.

In a further aspect, the present invention provides a method of treating atherosclerosis in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient about 5.0 mg of tirzepatide, or a pharmaceutically acceptable salt thereof, about once weekly for a minimum of about four weeks.

In another aspect, the present invention provides a method treating atherosclerosis in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a method treating atherosclerosis in a patient in need thereof comprising:

a) administering to said patient a maintenance dose of about 5.0 mg of tirzepatide, or a pharmaceutically acceptable salt thereof, about once weekly for a minimum of about four weeks; and thereafter
b) administering to said patient about 10.0 mg of tirzepatide, or a pharmaceutically acceptable salt thereof, about once weekly for a minimum of about four weeks.

Another embodiment provides a method treating atherosclerosis in a patient in need thereof comprising:
a) administering to said patient an escalation dose of about 7.5 mg of tirzepatide, or a pharmaceutically acceptable salt thereof, about once weekly for a minimum of about four weeks; and thereafter
b) administering to said patient about 10.0 mg of tirzepatide, or a pharmaceutically acceptable salt thereof, about once weekly for a minimum of about four weeks.

In another aspect, the present invention provides a method of treating atherosclerosis in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a method treating atherosclerosis in a patient in need thereof comprising:
a) administering to said patient a maintenance dose of about 10.0 mg of tirzepatide, or a pharmaceutically acceptable salt thereof, about once weekly for a minimum of about four weeks; and thereafter
b) administering to said patient about 15.0 mg of tirzepatide, or a pharmaceutically acceptable salt thereof, about once weekly for a minimum of about four weeks.

Another embodiment provides a method of treating atherosclerosis in a patient in need thereof, comprising:
a) administering to said patient an escalation dose of about 12.5 mg of tirzepatide, or a pharmaceutically acceptable salt thereof, about once weekly for a minimum of about four weeks; and thereafter
b) administering to said patient about 15.0 mg of tirzepatide, or a pharmaceutically acceptable salt thereof, about once weekly for a minimum of about four weeks.

In another aspect, the present invention provides a method of treating atherosclerosis in a patient in need thereof comprising:
a) administering to said patient an escalation dose of about 2.5 mg of tirzepatide, or a pharmaceutically acceptable salt thereof, about once weekly for a minimum of about four weeks; and thereafter
b) administering to said patient a maintenance dose of about 5.0 mg of tirzepatide, or a pharmaceutically acceptable salt thereof, about once weekly for a minimum of about four weeks; and thereafter
c) administering to said patient an escalation dose of about 7.5 mg of tirzepatide, or a pharmaceutically acceptable salt thereof, about once weekly for a minimum of about four weeks; and thereafter
d) administering to said patient a maintenance dose of about 10.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose.

In another aspect, the present invention provides a method of treating atherosclerosis in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient a maintenance dose of about 5.0 mg of tirzepatide, or a pharmaceutically acceptable salt thereof, about once weekly for a minimum of about four weeks; and thereafter
c) administering to said patient an escalation dose of about 7.5 mg of tirzepatide, or a pharmaceutically acceptable salt thereof, about once weekly for a minimum of about four weeks; and thereafter
d) administering to said patient a maintenance dose of about 10.0 mg of tirzepatide, or a pharmaceutically acceptable salt thereof, about once weekly for a minimum of about four weeks; and thereafter
e) administering to said patient an escalation dose of about 12.5 mg of tirzepatide, or a pharmaceutically acceptable salt thereof, about once weekly for a minimum of about four weeks; and thereafter
f) administering to said patient a maintenance dose of about 15.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose. In another aspect, the present invention includes a method as described in the preceding paragraph but which does not include administering the 12.5 mg escalation dose. In another aspect, the present invention includes a method as described in the preceding paragraph but which does not include administering the 7.5 mg and 12.5 mg escalation doses.

Also, the present invention provides a method of treating NAFLD in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof, and wherein the maintenance dose following an escalation dose is a 2.5 mg incremental relative to that escalation dose. An embodiment of the present invention for a method for treating NAFLD wherein the escalation dose administered about once weekly for at least about four weeks is about 2.5 mg and the maintenance dose administered about once weekly for at least about four weeks is about 5.0 mg. A further embodiment of the present invention is a method wherein the escalation dose administered about once weekly for at least about four weeks is about 7.5 mg and the maintenance dose administered about once weekly for at least about four weeks is about 10.0 mg. A further embodiment of the present invention is a method wherein the escalation dose administered about once weekly for at least about four weeks is about 12.5 mg and the maintenance dose administered about once weekly for at least about four weeks is about 15.0 mg. A further embodiment of the present invention is wherein the escalation doses administered about once weekly for at least about four weeks are about 2.5 mg and about 7.5 mg and the maintenance doses administered about once weekly for at least about four weeks are about 5.0 mg and about 10.0 mg. A further embodiment of the present invention is wherein the escalation doses administered about once weekly for at least about four weeks are about 2.5 mg, about 5.0 mg and about 7.5 mg and the maintenance doses administered about once weekly for at least about four weeks are about 5.0 mg, about 10.0 mg and about 15.0 mg.

Accordingly, the present invention provides a method of treating NAFLD in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient about 15.0 mg of tirzepatide, or a pharmaceutically acceptable salt thereof, about once weekly for a minimum of about four weeks.

In another aspect, the present invention provides a method of treating NAFLD in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a method of treating NAFLD in a patient in need thereof, comprising:
a) administering to said patient a maintenance dose of about 5.0 mg of tirzepatide, or a pharmaceutically acceptable salt thereof, about once weekly for a minimum of about four weeks; and thereafter
b) administering to said patient about 10.0 mg of tirzepatide, or a pharmaceutically acceptable salt thereof, about once weekly for a minimum of about four weeks.

Another embodiment provides a method of treating NAFLD in a patient in need thereof, comprising:
a) administering to said patient an escalation dose of about 7.5 mg of tirzepatide, or a pharmaceutically acceptable salt thereof, about once weekly for a minimum of about four weeks; and thereafter
b) administering to said patient about 10.0 mg of tirzepatide, or a pharmaceutically acceptable salt thereof, about once weekly for a minimum of about four weeks.

In another aspect, the present invention provides a method of treating NAFLD in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a method of treating NAFLD in a patient in need thereof, comprising:
a) administering to said patient a maintenance dose of about 10.0 mg of tirzepatide, or a pharmaceutically acceptable salt thereof, about once weekly for a minimum of about four weeks; and thereafter
b) administering to said patient about 15.0 mg of tirzepatide, or a pharmaceutically acceptable salt thereof, about once weekly for a minimum of about four weeks.

Another embodiment provides a method of treating NAFLD in a patient in need thereof, comprising:
a) administering to said patient an escalation dose of about 12.5 mg of tirzepatide, or a pharmaceutically acceptable salt thereof, about once weekly for a minimum of about four weeks; and thereafter b) administering to said patient about 15.0 mg of tirzepatide, or a pharmaceutically acceptable salt thereof, about once weekly for a minimum of about four weeks.

In another aspect, the present invention provides a method of treating NAFLD in a patient in need thereof, comprising: administering to said patient a dose of about 15.0 mg of tirzepatide, or a pharmaceutically acceptable salt thereof, about once weekly for a minimum of about four weeks.

In another aspect, the present invention provides a method of treating NAFLD in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient a maintenance dose of about 5.0 mg of tirzepatide, or a pharmaceutically acceptable salt thereof, about once weekly for a minimum of about four weeks; and thereafter
c) administering to said patient an escalation dose of about 7.5 mg of tirzepatide, or a pharmaceutically acceptable salt thereof, about once weekly for a minimum of about four weeks; and thereafter
d) administering to said patient a maintenance dose of about 10.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose.

In another aspect, the present invention provides a method of treating NAFLD in a patient in need thereof comprising:
a) administering to said patient an escalation dose of about 2.5 mg of tirzepatide, or a pharmaceutically acceptable salt thereof, about once weekly for a minimum of about four weeks; and thereafter
b) administering to said patient a maintenance dose of about 5.0 mg of tirzepatide, or a pharmaceutically acceptable salt thereof, about once weekly for a minimum of about four weeks; and thereafter
c) administering to said patient an escalation dose of about 7.5 mg of tirzepatide, or a pharmaceutically acceptable salt thereof, about once weekly for a minimum of about four weeks; and thereafter
d) administering to said patient a maintenance dose of about 10.0 mg of tirzepatide, or a pharmaceutically acceptable salt thereof, about once weekly for a minimum of about four weeks; and thereafter
e) administering to said patient an escalation dose of about 12.5 mg of tirzepatide, or a pharmaceutically acceptable salt thereof, about once weekly for a minimum of about four weeks; and thereafter
f) administering to said patient a maintenance dose of about 15.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose. In another aspect, the present invention includes a method as described in the preceding paragraph but which does not include administering the 12.5 mg escalation dose. In another aspect, the present invention includes a method as described in the preceding paragraph but which does not include administering the 7.5 mg and 12.5 mg escalation doses.

In an embodiment, is a method for treating dyslipidemia, in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof, and wherein the maintenance dose following an escalation dose is a 2.5 mg incremental increase relative to that escalation dose.

Also, the present invention provides a method of treating NASH in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof, and wherein the maintenance dose following an escalation dose is a 2.5 mg incremental increase relative to that escalation dose. An embodiment of the present invention for a method of treating NASH wherein the escalation dose administered about once weekly for at least about four weeks is about 2.5 mg and the maintenance dose administered about once weekly for at least about four weeks is about 5.0 mg. A further embodiment of the present invention is a method wherein the escalation dose administered about once weekly for at least about four weeks is about 7.5 mg and the maintenance dose administered about once weekly for at least about four weeks is about 10.0 mg. A further embodiment of the present invention is a method wherein the escalation dose administered about once weekly for at least about four weeks is about 12.5 mg and the maintenance dose administered about once weekly for at least about four weeks is about 15.0 mg. A further embodiment of the present invention is wherein the escalation doses administered about once weekly for at least about four weeks are about 2.5 mg and about 7.5 mg and the maintenance doses administered about once weekly for at least about four weeks are about 5.0 mg and about 10.0 mg. A further embodiment of the present invention is wherein the escalation doses administered about once weekly for at least about four weeks are about 2.5 mg, about 5.0 mg and about 7.5 mg and the maintenance doses administered about once weekly for at least about four weeks are about 5.0 mg, about 10.0 mg and about 15.0 mg.

Accordingly, the present invention provides a method of treating NASH in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient about 5.0 mg of tirzepatide, or a pharmaceutically acceptable salt thereof, about once weekly for a minimum of about four weeks.

In another aspect the present invention provides a method of treating NASH in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a method of treating NASH in a patient in need thereof, comprising:
a) administering to said patient a maintenance dose of about 5.0 mg of tirzepatide, or a pharmaceutically acceptable salt thereof, about once weekly for a minimum of about four weeks; and thereafter
b) administering to said patient about 10.0 mg of tirzepatide, or a pharmaceutically acceptable salt thereof, about once weekly for a minimum of about four weeks.

Another embodiment provides a method of treating NASH in a patient in need thereof, comprising:
a) administering to said patient an escalation dose of about 7.5 mg of tirzepatide, or a pharmaceutically acceptable salt thereof, about once weekly for a minimum of about four weeks; and thereafter
b) administering to said patient about 10.0 mg of tirzepatide, or a pharmaceutically acceptable salt thereof, about once weekly for a minimum of about four weeks.

In another aspect, the present invention provides a method of treating NASH in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a method of treating NASH in a patient in need thereof, comprising:
a) administering to said patient a maintenance dose of about 10.0 mg of tirzepatide, or a pharmaceutically acceptable salt thereof, about once weekly for a minimum of about four weeks; and thereafter
b) administering to said patient about 15.0 mg of tirzepatide, or a pharmaceutically acceptable salt thereof, about once weekly for a minimum of about four weeks.

Another embodiment provides a method of treating NASH in a patient in need thereof, comprising:
a) administering to said patient an escalation dose of about 12.5 mg of tirzepatide, or a pharmaceutically acceptable salt thereof, about once weekly for a minimum of about four weeks; and thereafter
b) administering to said patient about 15.0 mg of tirzepatide, or a pharmaceutically acceptable salt thereof, about once weekly for a minimum of about four weeks.

In another aspect, the present invention provides a method of treating NASH in a patient in need thereof, comprising: administering to said patient a maintenance dose of about 15.0 mg of tirzepatide, or a pharmaceutically acceptable salt thereof, about once weekly for a minimum of about four weeks.

In another aspect, the present invention provides a method of treating NASH in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient a maintenance dose of about 5.0 mg of tirzepatide, or a pharmaceutically acceptable salt thereof, about once weekly for a minimum of about four weeks; and thereafter
c) administering to said patient an escalation dose of about 7.5 mg of tirzepatide, or a pharmaceutically acceptable salt thereof, about once weekly for a minimum of about four weeks; and thereafter
d) administering to said patient a maintenance dose of about 10.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose.

In another aspect, the present invention provides a method of treating NASH in a patient in need thereof comprising:
a) administering to said patient an escalation dose of about 2.5 mg of tirzepatide, or a pharmaceutically acceptable salt thereof, about once weekly for a minimum of about four weeks; and thereafter
b) administering to said patient a maintenance dose of about 5.0 mg of tirzepatide, or a pharmaceutically acceptable salt thereof, about once weekly for a minimum of about four weeks; and thereafter
c) administering to said patient an escalation dose of about 7.5 mg of tirzepatide, or a pharmaceutically acceptable salt thereof, about once weekly for a minimum of about four weeks; and thereafter
d) administering to said patient a maintenance dose of about 10.0 mg of tirzepatide, or a pharmaceutically acceptable salt thereof, about once weekly for a minimum of about four weeks; and thereafter
e) administering to said patient an escalation dose of about 12.5 mg of tirzepatide, or a pharmaceutically acceptable salt thereof, about once weekly for a minimum of about four weeks; and thereafter
f) administering to said patient a maintenance dose of about 15.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose. In another aspect, the present invention includes a method as described in the preceding paragraph but which does not include administering the 12.5 mg escalation dose. In another aspect, the present invention includes a method as described in the preceding paragraph but which does not include administering the 7.5 mg and 12.5 mg escalation doses.

Also, the present invention provides a method to cure diabetes, induce remission or regression of diabetes, or prevent diabetes in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose. An embodiment of the present invention for a method to cure diabetes, induce remission or regression of diabetes, or prevent diabetes wherein the escalation dose administered about once weekly for at least about four weeks is about 2.5 mg and the maintenance dose administered about once weekly for at least about four weeks is about 5.0 mg. A further embodiment of the present invention is a method wherein the escalation dose administered about once weekly for at least about four weeks is about 7.5 mg and the maintenance dose administered about once weekly for at least about four weeks is about 10.0 mg. A further embodiment of the present invention is a method wherein the escalation dose administered about once weekly for at least about four weeks is about 12.5 mg and the maintenance dose administered about once weekly for at least about four weeks is about 15.0 mg. A further embodiment of the present invention is wherein the escalation doses administered about once weekly for at least about four weeks are about 2.5 mg and about 7.5 mg and the maintenance doses administered about once weekly for at least about four weeks are about 5.0 mg and about 10.0 mg. A further embodiment of the present invention is wherein the escalation doses administered about once weekly for at least about four weeks are about 2.5 mg, about 5.0 mg and about 7.5 mg and the maintenance doses administered about once weekly for at least about four weeks are about 5.0 mg, about 10.0 mg and about 15.0 mg.

Accordingly, the present invention provides a method to cure diabetes, induce remission or regression of diabetes, or prevent diabetes in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient about 5.0 mg of tirzepatide, or a pharmaceutically acceptable salt thereof, about once weekly for a minimum of about four weeks.

In another aspect, the present invention provides a method to cure diabetes, induce remission or regression of diabetes, or prevent diabetes in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a method to cure diabetes, induce remission or regression of diabetes, or prevent diabetes in a patient in need thereof, comprising:
a) administering to said patient a maintenance dose of about 5.0 mg of tirzepatide, or a pharmaceutically acceptable salt thereof, about once weekly for a minimum of about four weeks; and thereafter
b) administering to said patient about 10.0 mg of tirzepatide, or a pharmaceutically acceptable salt thereof, about once weekly for a minimum of about four weeks.

Another embodiment provides a method to cure diabetes, induce remission or regression of diabetes, or prevent diabetes in a patient in need thereof, comprising:
a) administering to said patient an escalation dose of about 7.5 mg of tirzepatide, or a pharmaceutically acceptable salt thereof, about once weekly for a minimum of about four weeks; and thereafter
b) administering to said patient about 10.0 mg of tirzepatide, or a pharmaceutically acceptable salt thereof, about once weekly for a minimum of about four weeks.

In another aspect, the present invention provides a method to cure diabetes, induce remission or regression of diabetes, or prevent diabetes in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a method to cure diabetes, induce remission or regression of diabetes, or prevent diabetes in a patient in need thereof, comprising:
a) administering to said patient a maintenance dose of about 10.0 mg of tirzepatide, or a pharmaceutically acceptable salt thereof, about once weekly for a minimum of about four weeks; and thereafter
b) administering to said patient about 15.0 mg of tirzepatide, or a pharmaceutically acceptable salt thereof, about once weekly for a minimum of about four weeks.

Another embodiment provides a method to cure diabetes, induce remission or regression of diabetes, or prevent diabetes in a patient in need thereof, comprising:
a) administering to said patient an escalation dose of about 12.5 mg of tirzepatide, or a pharmaceutically acceptable salt thereof, about once weekly for a minimum of about four weeks; and thereafter
b) administering to said patient about 15.0 mg of tirzepatide, or a pharmaceutically acceptable salt thereof, about once weekly for a minimum of about four weeks.

In another aspect, the present invention provides a method to cure diabetes, induce remission or regression of diabetes, or prevent diabetes in a patient in need thereof, comprising: administering to said patient a maintenance dose of about 15.0 mg of tirzepatide, or a pharmaceutically acceptable salt thereof, about once weekly for a minimum of about four weeks.

In another aspect, the present invention provides a method to cure diabetes, induce remission or regression of diabetes, or prevent diabetes in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient a maintenance dose of about 5.0 mg of tirzepatide, or a pharmaceutically acceptable salt thereof, about once weekly for a minimum of about four weeks; and thereafter
c) administering to said patient an escalation dose of about 7.5 mg of tirzepatide, or a pharmaceutically acceptable salt thereof, about once weekly for a minimum of about four weeks; and thereafter
d) administering to said patient a maintenance dose of about 10.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose.

In another aspect, the present invention provides a method to cure diabetes, induce remission or regression of diabetes, or prevent diabetes in a patient in need thereof comprising:
a) administering to said patient an escalation dose of about 2.5 mg of tirzepatide, or a pharmaceutically acceptable salt thereof, about once weekly for a minimum of about four weeks; and thereafter
b) administering to said patient a maintenance dose of about 5.0 mg of tirzepatide, or a pharmaceutically acceptable salt thereof, about once weekly for a minimum of about four weeks; and thereafter
c) administering to said patient an escalation dose of about 7.5 mg of tirzepatide, or a pharmaceutically acceptable salt thereof, about once weekly for a minimum of about four weeks; and thereafter
d) administering to said patient a maintenance dose of about 10.0 mg of tirzepatide, or a pharmaceutically acceptable salt thereof, about once weekly for a minimum of about four weeks; and thereafter e) administering to said patient an escalation dose of about 12.5 mg of tirzepatide, or a pharmaceutically acceptable salt thereof, about once weekly for a minimum of about four weeks; and thereafter f) administering to said patient a maintenance dose of about 15.0 mg of tirzepatide, or a pharmaceutically acceptable salt thereof, about once weekly for a minimum of about four weeks.

In another aspect, the present invention includes a method as described in the preceding paragraph but which does not include administering the 7.5 mg escalation dose. In another aspect, the present invention includes a method as described in the preceding paragraph but which does not include administering the 12.5 mg escalation dose. In another aspect, the present invention includes a method as described in the preceding paragraph but which does not include administering the 7.5 mg and 12.5 mg escalation doses.

Furthermore, the present invention provides a use of tirzepatide, or a pharmaceutically acceptable salt thereof, in the manufacture of a medicament for treating type 2 diabetes in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof: wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose.

The present invention provides a use of tirzepatide, or a pharmaceutically acceptable salt thereof, in the manufacture of a medicament for treating type 2 diabetes in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient about 5.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating type 2 diabetes in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating type 2 diabetes in a patient in need thereof, comprising:
a) administering to said patient a maintenance dose of about 5.0 mg of tirzepatide, or a pharmaceutically acceptable salt thereof, about once weekly for a minimum of about four weeks; and thereafter
b) administering to said patient about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating type 2 diabetes in a patient in need thereof; comprising:
a) administering to said patient an escalation dose of about 7.5 mg of tirzepatide, or a pharmaceutically acceptable salt thereof, about once weekly for a minimum of about four weeks; and thereafter
b) administering to said patient about 10.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating type 2 diabetes in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating type 2 diabetes in a patient in need thereof, comprising:
a) administering to said patient a maintenance dose of about 10.0 mg of tirzepatide, or a pharmaceutically acceptable salt thereof, about once weekly for a minimum of about four weeks; and thereafter
b) administering to said patient about 15.0 mg of tirzepatide, or a pharmaceutically acceptable salt thereof, about once weekly for a minimum of about four weeks.

Another embodiment provides a use of tirzepatide, or a pharmaceutically acceptable salt thereof, in manufacture of a medicament for treating type 2 diabetes in a patient in need thereof, comprising:
a) administering to said patient an escalation dose of about 12.5 mg of tirzepatide, or a pharmaceutically acceptable salt thereof, about once weekly for a minimum of about four weeks; and thereafter
b) administering to said patient about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating type 2 diabetes in a patient in need thereof, comprising: administering to said patient a maintenance dose of about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating type 2 diabetes in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient a maintenance dose of about 5.0 mg of tirzepatide, or a pharmaceutically acceptable salt thereof, about once weekly for a minimum of about four weeks; and thereafter
c) administering to said patient an escalation dose of about 7.5 mg of tirzepatide, or a pharmaceutically acceptable salt thereof, about once weekly for a minimum of about four weeks; and thereafter d) administering to said patient a maintenance dose of about 10.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose.

In another aspect the present invention provides a use of tirzepatide, or a pharmaceutically acceptable salt thereof, in the manufacture of a medicament for treating type 2 diabetes in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient a maintenance dose of about 5.0 mg of tirzepatide, or a pharmaceutically acceptable salt thereof, about once weekly for a minimum of about four weeks; and thereafter
c) administering to said patient an escalation dose of about 7.5 mg of tirzepatide, or a pharmaceutically acceptable salt thereof, about once weekly for a minimum of about four weeks; and thereafter
d) administering to said patient a maintenance dose of about 10.0 mg of tirzepatide, or a pharmaceutically acceptable salt thereof, about once weekly for a minimum of about four weeks; and thereafter
e) administering to said patient an escalation dose of about 12.5 mg of tirzepatide, or a pharmaceutically acceptable salt thereof, about once weekly for a minimum of about four weeks; and thereafter
f) administering to said patient a maintenance dose of about 15.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose. In another aspect, the present invention includes a medicament as described in the preceding paragraph but which does not include administering the 12.5 mg escalation dose. In another aspect, the present invention includes a medicament as described in the preceding paragraph but which does not include administering the 7.5 mg and 12.5 mg escalation doses.

Furthermore, the present invention provides a use of tirzepatide, or a pharmaceutically acceptable salt thereof, in the manufacture of a medicament in improving glycemic control in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof, and wherein the maintenance dose following an escalation dose is a 2.5 mg incremental increase relative to that escalation dose.

Furthermore, the present invention provides a use of tirzepatide, or a pharmaceutically acceptable salt thereof, in the manufacture of a medicament for improving glycemic control in a patient in need thereof, comprising:
a) administering to said patient an escalation dose of about 2.5 mg of tirzepatide, or a pharmaceutically acceptable salt thereof, about once weekly for a minimum of about four weeks; and thereafter
b) administering to said patient about 5.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for improving glycemic control in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for improving glycemic control in a patient in need thereof, comprising:
a) administering to said patient an escalation dose of about 5.0 mg of tirzepatide, or a pharmaceutically acceptable salt thereof, about once weekly for a minimum of about four weeks; and thereafter
b) administering to said patient about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for improving glycemic control in a patient in need thereof, comprising:
a) administering to said patient an escalation dose of about 7.5 mg of tirzepatide, or a pharmaceutically acceptable salt thereof, about once weekly for a minimum of about four weeks; and thereafter
b) administering to said patient about 10.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for improving glycemic control in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for improving glycemic control in a patient in need thereof, comprising:
a) administering to said patient a maintenance dose of about 10.0 mg of tirzepatide, or a pharmaceutically acceptable salt thereof, about once weekly for a minimum of about four weeks; and thereafter
b) administering to said patient about 15.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for improving glycemic control in a patient in need thereof, comprising:
a) administering to said patient an escalation dose of about 12.5 mg of tirzepatide, or a pharmaceutically acceptable salt thereof, about once weekly for a minimum of about four weeks; and thereafter b) administering to said patient about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for improving glycemic control in a patient in need thereof, comprising: administering to said patient a maintenance dose of about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for improving glycemic control in a patient in need thereof, comprising:
 a) administering to said patient an escalation dose of about 2.5 mg of tirzepatide, or a pharmaceutically acceptable salt thereof, about once weekly for a minimum of about four weeks; and thereafter
 b) administering to said patient a maintenance dose of about 5.0 mg of tirzepatide, or a pharmaceutically acceptable salt thereof, about once weekly for a minimum of about four weeks; and thereafter
 c) administering to said patient an escalation dose of about 7.5 mg of tirzepatide, or a pharmaceutically acceptable salt thereof, about once weekly for a minimum of about four weeks; and thereafter
 d) administering to said patient a maintenance dose of about 10.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose.

In another aspect, the present invention provides a use of tirzepatide, or a pharmaceutically acceptable salt thereof, in the manufacture of a medicament for improving glycemic control in a patient in need thereof, comprising:
 a) administering to said patient an escalation dose of about 2.5 mg of tirzepatide, or a pharmaceutically acceptable salt thereof, about once weekly for a minimum of about four weeks; and thereafter
 b) administering to said patient a maintenance dose of about 5.0 mg of tirzepatide, or a pharmaceutically acceptable salt thereof, about once weekly for a minimum of about four weeks; and thereafter
 c) administering to said patient an escalation dose of about 7.5 mg of tirzepatide, or a pharmaceutically acceptable salt thereof, about once weekly for a minimum of about four weeks; and thereafter
 d) administering to said patient a maintenance dose of about 10.0 mg of tirzepatide, or a pharmaceutically acceptable salt thereof, about once weekly for a minimum of about four weeks; and thereafter
 e) administering to said patient an escalation dose of about 12.5 mg of tirzepatide, or a pharmaceutically acceptable salt thereof, about once weekly for a minimum of about four weeks; and thereafter
 f) administering to said patient a maintenance dose of about 15.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose. In another aspect, the present invention includes a medicament as described in the preceding paragraph but which does not include administering the 12.5 mg escalation dose. In another aspect, the present invention includes a medicament as described in the preceding paragraph but which does not include administering the 7.5 mg and 12.5 mg escalation doses.

Furthermore, present invention provides a use of tirzepatide, or a pharmaceutically acceptable salt thereof, in the manufacture of a medicament in improving weight management in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose.

In yet another aspect, the present invention provides a use of tirzepatide, or a pharmaceutically acceptable salt thereof, in the manufacture of a medicament for improving weight management in a patient in need thereof, comprising:
 a) administering to said patient an escalation dose of about 2.5 mg of tirzepatide, or a pharmaceutically acceptable salt thereof, about once weekly for a minimum of about four weeks; and thereafter
 b) administering to said patient about 5.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for improving weight management in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for improving weight management in a patient in need thereof, comprising:
 a) administering to said patient a maintenance dose of about 5.0 mg of tirzepatide, or a pharmaceutically acceptable salt thereof, about once weekly for a minimum of about four weeks; and thereafter
 b) administering to said patient about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for improving weight management in a patient in need thereof, comprising:
 a) administering to said patient an escalation dose of about 7.5 mg of tirzepatide, or a pharmaceutically acceptable salt thereof, about once weekly for a minimum of about four weeks; and thereafter
 b) administering to said patient about 10.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for improving weight management in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for improving weight management in a patient in need thereof, comprising:
  a) administering to said patient a maintenance dose of about 10.0 mg of tirzepatide, or a pharmaceutically acceptable salt thereof, about once weekly for a minimum of about four weeks; and thereafter
  b) administering to said patient about 15.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for improving weight management in a patient in need thereof, comprising:
  a) administering to said patient an escalation dose of about 12.5 mg of tirzepatide, or a pharmaceutically acceptable salt thereof, about once weekly for a minimum of about four weeks; and thereafter
  b) administering to said patient about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for improving weight management in a patient in need thereof, comprising: administering to said patient a maintenance dose of about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for improving weight management in a patient in need thereof, comprising:
  a) administering to said patient an escalation dose of about 2.5 mg of tirzepatide, or a pharmaceutically acceptable salt thereof, about once weekly for a minimum of about four weeks; and thereafter
  b) administering to said patient a maintenance dose of about 5.0 mg of tirzepatide, or a pharmaceutically acceptable salt thereof, about once weekly for a minimum of about four weeks; and thereafter
  c) administering to said patient an escalation dose of about 7.5 mg of tirzepatide, or a pharmaceutically acceptable salt thereof, about once weekly for a minimum of about four weeks; and thereafter
  d) administering to said patient a maintenance dose of about 10.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose.

In another aspect, the present invention provides a use of tirzepatide, or a pharmaceutically acceptable salt thereof, in the manufacture of a medicament for improving weight management in a patient in need thereof, comprising:
  a) administering to said patient an escalation dose of about 2.5 mg of tirzepatide, or a pharmaceutically acceptable salt thereof, about once weekly for a minimum of about four weeks; and thereafter
  b) administering to said patient a maintenance dose of about 5.0 mg of tirzepatide, or a pharmaceutically acceptable salt thereof, about once weekly for a minimum of about four weeks; and thereafter
  c) administering to said patient an escalation dose of about 7.5 mg of tirzepatide, or a pharmaceutically acceptable salt thereof, about once weekly for a minimum of about four weeks; and thereafter
  d) administering to said patient a maintenance dose of about 10.0 mg of tirzepatide, or a pharmaceutically acceptable salt thereof, about once weekly for a minimum of about four weeks; and thereafter
  e) administering to said patient an escalation dose of about 12.5 mg of tirzepatide, or a pharmaceutically acceptable salt thereof, about once weekly for a minimum of about four weeks; and thereafter
  f) administering to said patient a maintenance dose of about 15.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose. In another aspect, the present invention includes a medicament as described in the preceding paragraph but which does not include administering the 12.5 mg escalation dose. In another aspect, the present invention includes a medicament as described in the preceding paragraph but which does not include administering the 7.5 mg and 12.5 mg escalation doses.

Furthermore, the present invention provides a use of tirzepatide, or a pharmaceutically acceptable salt thereof, in the manufacture of a medicament for treating chronic kidney disease in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose.

The present invention provides a use of tirzepatide, or a pharmaceutically acceptable salt thereof, in the manufacture of a medicament for treating chronic kidney disease in a patient in need thereof, comprising:
  a) administering to said patient an escalation dose of about 2.5 mg of tirzepatide, or a pharmaceutically acceptable salt thereof, about once weekly for a minimum of about four weeks; and thereafter
  b) administering to said patient about 5.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating chronic kidney disease in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating chronic kidney disease in a patient in need thereof, comprising:
- a) administering to said patient a maintenance dose of about 5.0 mg of tirzepatide, or a pharmaceutically acceptable salt thereof, about once weekly for a minimum of about four weeks; and thereafter
- b) administering to said patient about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating chronic kidney disease in a patient in need thereof, comprising:
- a) administering to said patient an escalation dose of about 7.5 mg of tirzepatide, or a pharmaceutically acceptable salt thereof, about once weekly for a minimum of about four weeks; and thereafter
- b) administering to said patient about 10.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating chronic kidney disease in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating chronic kidney disease in a patient in need thereof, comprising:
- a) administering to said patient a maintenance dose of about 10.0 mg of tirzepatide, or a pharmaceutically acceptable salt thereof, about once weekly for a minimum of about four weeks; and thereafter
- b) administering to said patient about 15.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating chronic kidney disease in a patient in need thereof, comprising:
- a) administering to said patient an escalation dose of about 12.5 mg of tirzepatide, or a pharmaceutically acceptable salt thereof, about once weekly for a minimum of about four weeks; and thereafter
- b) administering to said patient about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating chronic kidney disease in a patient in need thereof, comprising: administering to said patient a maintenance dose of about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating chronic kidney disease in a patient in need thereof, comprising:
- a) administering to said patient an escalation dose of about 2.5 mg of tirzepatide, or a pharmaceutically acceptable salt thereof, about once weekly for a minimum of about four weeks; and thereafter
- b) administering to said patient a maintenance dose of about 5.0 mg of tirzepatide, or a pharmaceutically acceptable salt thereof, about once weekly for a minimum of about four weeks; and thereafter
- c) administering to said patient an escalation dose of about 7.5 mg of tirzepatide, or a pharmaceutically acceptable salt thereof, about once weekly for a minimum of about four weeks; and thereafter
- d) administering to said patient a maintenance dose of about 10.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose.

In another aspect, the present invention provides a use of tirzepatide, or a pharmaceutically acceptable salt thereof, in the manufacture of a medicament for treating chronic kidney disease in a patient in need thereof, comprising:
- a) administering to said patient an escalation dose of about 2.5 mg of tirzepatide, or a pharmaceutically acceptable salt thereof, about once weekly for a minimum of about four weeks; and thereafter
- b) administering to said patient a maintenance dose of about 5.0 mg of tirzepatide, or a pharmaceutically acceptable salt thereof, about once weekly for a minimum of about four weeks; and thereafter
- c) administering to said patient an escalation dose of about 7.5 mg of tirzepatide, or a pharmaceutically acceptable salt thereof, about once weekly for a minimum of about four weeks; and thereafter
- d) administering to said patient a maintenance dose of about 10.0 mg of tirzepatide, or a pharmaceutically acceptable salt thereof, about once weekly for a minimum of about four weeks; and thereafter
- e) administering to said patient an escalation dose of about 12.5 mg of tirzepatide, or a pharmaceutically acceptable salt thereof, about once weekly for a minimum of about four weeks; and thereafter
- f) administering to said patient a maintenance dose of about 15.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose. In another aspect, the present invention includes a medicament as described in the preceding paragraph but which does not include administering the 12.5 mg escalation dose. In another aspect, the present invention includes a medicament as described in the preceding paragraph but which does not include administering the 7.5 mg and 12.5 mg escalation doses.

In a further embodiment, the present invention provides a use of tirzepatide, or a pharmaceutically acceptable salt thereof, in the manufacture of a medicament for treating diabetic kidney disease in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof, and wherein the maintenance dose following an escalation dose is a 2.5 mg incremental increase relative to that escalation dose.

Furthermore, present invention provides a use of tirzepatide, or a pharmaceutically acceptable salt thereof, in the manufacture of a medicament for treating atherosclerosis in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof, and wherein the maintenance dose following an escalation dose is a 2.5 mg incremental increase relative to that escalation dose.

Furthermore, the present invention provides a use of tirzepatide, or a pharmaceutically acceptable salt thereof, in the manufacture of a medicament for treating atherosclerosis in a patient in need thereof, comprising:
  a) administering to said patient an escalation dose of about 2.5 mg of tirzepatide, or a pharmaceutically acceptable salt thereof, about once weekly for a minimum of about four weeks; and thereafter
  b) administering to said patient about 5.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating atherosclerosis in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating atherosclerosis in a patient in need thereof, comprising:
  a) administering to said patient a maintenance dose of about 5.0 mg of tirzepatide, or a pharmaceutically acceptable salt thereof, about once weekly for a minimum of about four weeks; and thereafter
  b) administering to said patient about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating atherosclerosis in a patient in need thereof, comprising:
  a) administering to said patient an escalation dose of about 7.5 mg of tirzepatide, or a pharmaceutically acceptable salt thereof, about once weekly for a minimum of about four weeks; and thereafter
  b) administering to said patient about 10.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating atherosclerosis in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating atherosclerosis in a patient in need thereof, comprising:
  a) administering to said patient a maintenance dose of about 10.0 mg of tirzepatide, or a pharmaceutically acceptable salt thereof, about once weekly for a minimum of about four weeks; and thereafter
  b) administering to said patient about 15.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating atherosclerosis in a patient in need thereof, comprising:
  a) administering to said patient an escalation dose of about 12.5 mg of tirzepatide, or a pharmaceutically acceptable salt thereof, about once weekly for a minimum of about four weeks; and
  b) administering to said patient about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating atherosclerosis in a patient in need thereof, comprising: administering to said patient a maintenance dose of about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating atherosclerosis in a patient in need thereof, comprising:
  a) administering to said patient an escalation dose of about 2.5 mg of tirzepatide, or a pharmaceutically acceptable salt thereof, about once weekly for a minimum of about four weeks; and thereafter
  b) administering to said patient a maintenance dose of about 5.0 mg of tirzepatide, or a pharmaceutically acceptable salt thereof, about once weekly for a minimum of about four weeks; and thereafter
  c) administering to said patient an escalation dose of about 7.5 mg of tirzepatide, or a pharmaceutically acceptable salt thereof, about once weekly for a minimum of about four weeks; and thereafter
  d) administering to said patient a maintenance dose of about 10.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose. In another aspect, the present invention provides a use of tirzepatide, or a pharmaceutically acceptable salt thereof, in the manufacture of a medicament for treating atherosclerosis in a patient in need thereof, comprising:
  a) administering to said patient an escalation dose of about 2.5 mg of tirzepatide, or a pharmaceutically acceptable salt thereof, about once weekly for a minimum of about four weeks; and thereafter b) administering to said patient a maintenance dose of about 5.0 mg of tirzepatide, or a pharmaceutically acceptable salt thereof, about once weekly for a minimum of about four weeks; and thereafter c) administering to said patient an escalation dose of about 7.5 mg of tirzepatide, or a pharmaceutically acceptable salt thereof, about once weekly for a minimum of about four weeks; and thereafter d) administering to said patient a maintenance dose of about 10.0 mg of tirzepatide, or a pharmaceutically acceptable salt thereof, about once weekly for a minimum of about four weeks; and thereafter e) administering to said patient an escalation dose of about 12.5 mg of tirzepatide, or a pharmaceutically acceptable salt thereof, about once weekly for a minimum of about four weeks; and thereafter f) administering to said patient a maintenance dose of about 15.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose. In another aspect, the present invention includes a medicament as described in the preceding paragraph but which does not include administering the 12.5 mg escalation dose. In another aspect, the present invention includes a medicament as described in the preceding paragraph but which does not include administering the 7.5 mg and 12.5 mg escalation doses.

In an embodiment is method of treating dyslipidemia in a patient in need thereof, comprising: administering an escalation dose about once weekly for a minimum of at least about two weeks and thereafter administering a maintenance dose about once weekly for a minimum of at least about two weeks; wherein the escalation dose is selected from the group consisting of about 2.5 mg, about 7.5 mg and about 12.5 mg of tirzepatide, or a pharmaceutically acceptable salt thereof; and wherein the maintenance dose is selected from the group consisting of about 5.0 mg, about 10.0 mg and about 15.0 mg of tirzepatide, or a pharmaceutically acceptable salt thereof.

In an embodiment is a method for treating dyslipidemia in a patient in need thereof, comprising: administering at least one escalation dose about once weekly for a minimum of about four weeks and at least one maintenance dose about once weekly for a minimum of about four weeks following the escalation dose; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg increment.

In an embodiment is a method for treating dyslipidemia, wherein the escalation dose is about 2.5 mg and the maintenance dose is about 5.0 mg.

In an embodiment is a method for treating dyslipidemia, wherein the escalation dose is about 7.5 mg and the maintenance dose is about 10.0 mg.

In an embodiment is a method for treating dyslipidemia, wherein the escalation dose is about 12.5 mg and the maintenance dose is about 15.0 mg.

In an embodiment is a method for treating dyslipidemia, further comprising an escalation dose of about 7.5 mg and a maintenance dose of about 10.0 mg.

In an embodiment is a method for treating dyslipidemia, further comprising an escalation dose of about 12.5 mg and a maintenance dose of about 15.0 mg.

In an embodiment is a method for treating dyslipidemia, wherein the patient in need of such treatment does not have comorbid type 1 or type 2 diabetes.

Furthermore, present invention provides a use of tirzepatide, or a pharmaceutically acceptable salt thereof, in the manufacture of a medicament for treating NALFD in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof, and wherein the maintenance dose following an escalation dose is a 2.5 mg incremental increase relative to that escalation dose.

In yet another aspect, the present invention provides a use of tirzepatide, or a pharmaceutically acceptable salt thereof, in the manufacture of a medicament for treating NAFLD in a patient in need thereof, comprising:

a) administering to said patient an escalation dose of about 2.5 mg of tirzepatide, or a pharmaceutically acceptable salt thereof, about once weekly for a minimum of about four weeks; and thereafter b) administering to said patient about 5.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating NAFLD in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating NAFLD in a patient in need thereof, comprising:

a) administering to said patient a maintenance dose of about 5.0 mg of tirzepatide, or a pharmaceutically acceptable salt thereof, about once weekly for a minimum of about four weeks; and thereafter b) administering to said patient about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating NAFLD in a patient in need thereof, comprising:

a) administering to said patient an escalation dose of about 7.5 mg of tirzepatide, or a pharmaceutically acceptable salt thereof, about once weekly for a minimum of about four weeks; and thereafter b) administering to said patient about 10.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating NAFLD in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating NAFLD in a patient in need thereof, comprising:
- a) administering to said patient a maintenance dose of about 10.0 mg of tirzepatide, or a pharmaceutically acceptable salt thereof, about once weekly for a minimum of about four weeks; and thereafter
- b) administering to said patient about 15.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating NAFLD in a patient in need thereof, comprising:
- a) administering to said patient an escalation dose of about 12.5 mg of tirzepatide, or a pharmaceutically acceptable salt thereof, about once weekly for a minimum of about four weeks; and thereafter
- b) administering to said patient about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating NAFLD in a patient in need thereof, comprising: administering to said patient a maintenance dose of about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating NAFLD in a patient in need thereof, comprising:
- a) administering to said patient an escalation dose of about 2.5 mg of tirzepatide, or a pharmaceutically acceptable salt thereof, about once weekly for a minimum of about four weeks; and thereafter
- b) administering to said patient a maintenance dose of about 5.0 mg of tirzepatide, or a pharmaceutically acceptable salt thereof, about once weekly for a minimum of about four weeks; and thereafter
- c) administering to said patient an escalation dose of about 7.5 mg of tirzepatide, or a pharmaceutically acceptable salt thereof, about once weekly for a minimum of about four weeks; and thereafter
- d) administering to said patient a maintenance dose of about 10.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose.

In another aspect, the present invention provides a use of tirzepatide, or a pharmaceutically acceptable salt thereof, in the manufacture of a medicament for treating NAFLD in a patient in need thereof, comprising:
- a) administering to said patient an escalation dose of about 2.5 mg of tirzepatide, or a pharmaceutically acceptable salt thereof, about once weekly for a minimum of about four weeks; and thereafter
- b) administering to said patient a maintenance dose of about 5.0 mg of tirzepatide, or a pharmaceutically acceptable salt thereof, about once weekly for a minimum of about four weeks; and thereafter
- c) administering to said patient an escalation dose of about 7.5 mg of tirzepatide, or a pharmaceutically acceptable salt thereof, about once weekly for a minimum of about four weeks; and thereafter
- d) administering to said patient a maintenance dose of about 10.0 mg of tirzepatide, or a pharmaceutically acceptable salt thereof, about once weekly for a minimum of about four weeks; and thereafter
- e) administering to said patient an escalation dose of about 12.5 mg of tirzepatide, or a pharmaceutically acceptable salt thereof, about once weekly for a minimum of about four weeks; and thereafter
- f) administering to said patient a maintenance dose of about 15.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose. In another aspect, the present invention includes a medicament as described in the preceding paragraph but which does not include administering the 12.5 mg escalation dose. In another aspect, the present invention includes a medicament as described in the preceding paragraph but which does not include administering the 7.5 mg and 12.5 mg escalation doses.

Furthermore, present invention provides a use of tirzepatide, or a pharmaceutically acceptable salt thereof, in the manufacture of a medicament for treating NASH in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof, and wherein the maintenance dose following an escalation dose is a 2.5 mg incremental increase relative to that escalation dose.

The present invention provides a use of tirzepatide, or a pharmaceutically acceptable salt thereof, in the manufacture of a medicament for treating NASH in a patient in need thereof, comprising:
- a) administering to said patient an escalation dose of about 2.5 mg of tirzepatide, or a pharmaceutically acceptable salt thereof, about once weekly for a minimum of about four weeks; and thereafter
- b) administering to said patient about 5.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating NASH in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating NASH in a patient in need thereof, comprising:
- a) administering to said patient a maintenance dose of about 5.0 mg of tirzepatide, or a pharmaceutically acceptable salt thereof, about once weekly for a minimum of about four weeks; and thereafter
- b) administering to said patient about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating NASH in a patient in need thereof, comprising:
- a) administering to said patient an escalation dose of about 7.5 mg of tirzepatide, or a pharmaceutically acceptable salt thereof, about once weekly for a minimum of about four weeks; and thereafter
- b) administering to said patient about 10.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating NASH in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating NASH in a patient in need thereof, comprising:
- a) administering to said patient a maintenance dose of about 10.0 mg of tirzepatide, or a pharmaceutically acceptable salt thereof, about once weekly for a minimum of about four weeks; and thereafter
- b) administering to said patient about 15.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament for treating NASH in a patient in need thereof, comprising:
- a) administering to said patient an escalation dose of about 12.5 mg of tirzepatide, or a pharmaceutically acceptable salt thereof, about once weekly for a minimum of about four weeks; and thereafter
- b) administering to said patient about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating NASH in a patient in need thereof, comprising: administering to said patient a maintenance dose of about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament for treating NASH thereof, comprising:
- a) administering to said patient an escalation dose of about 2.5 mg of tirzepatide, or a pharmaceutically acceptable salt thereof, about once weekly for a minimum of about four weeks; and thereafter
- b) administering to said patient a maintenance dose of about 5.0 mg of tirzepatide, or a pharmaceutically acceptable salt thereof, about once weekly for a minimum of about four weeks; and thereafter
- c) administering to said patient an escalation dose of about 7.5 mg of tirzepatide, or a pharmaceutically acceptable salt thereof, about once weekly for a minimum of about four weeks; and thereafter
- d) administering to said patient a maintenance dose of about 10.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose.

In another aspect, the present invention provides a use of tirzepatide, or a pharmaceutically acceptable salt thereof, in the manufacture of a medicament for treating NASH in a patient in need thereof, comprising:
- a) administering to said patient an escalation dose of about 2.5 mg of tirzepatide, or a pharmaceutically acceptable salt thereof, about once weekly for a minimum of about four weeks; and thereafter
- b) administering to said patient a maintenance dose of about 5.0 mg of tirzepatide, or a pharmaceutically acceptable salt thereof, about once weekly for a minimum of about four weeks; and thereafter
- c) administering to said patient an escalation dose of about 7.5 mg of tirzepatide, or a pharmaceutically acceptable salt thereof, about once weekly for a minimum of about four weeks; and thereafter
- d) administering to said patient a maintenance dose of about 10.0 mg of tirzepatide, or a pharmaceutically acceptable salt thereof, about once weekly for a minimum of about four weeks; and thereafter
- e) administering to said patient an escalation dose of about 12.5 mg of tirzepatide, or a pharmaceutically acceptable salt thereof, about once weekly for a minimum of about four weeks; and thereafter
- f) administering to said patient a maintenance dose of about 15.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose. In another aspect, the present invention includes a medicament as described in the preceding paragraph but which does not include administering the 12.5 mg escalation dose. In another aspect, the present invention includes a medicament as described in the preceding paragraph but which does not include administering the 7.5 mg and 12.5 mg escalation doses.

Furthermore, the present invention provides a use of tirzepatide, or a pharmaceutically acceptable salt thereof, in the manufacture of a medicament to cure diabetes, induce remission or regression of diabetes, or prevent diabetes in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof, and wherein the maintenance dose following an escalation dose is a 2.5 mg incremental increase relative to that escalation dose.

The present invention provides a use of tirzepatide, or a pharmaceutically acceptable salt thereof, in the manufacture of a medicament to cure diabetes, induce remission or regression of diabetes, or prevent diabetes in a patient in need thereof, comprising:
  a) administering to said patient an escalation dose of about 2.5 mg of tirzepatide, or a pharmaceutically acceptable salt thereof, about once weekly for a minimum of about four weeks; and thereafter
  b) administering to said patient about 5.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament to cure diabetes, induce remission or regression of diabetes, or prevent diabetes in a patient in need thereof, comprising: administering to said patient a maintenance dose of about 5.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament to cure diabetes, induce remission or regression of diabetes, or prevent diabetes in a patient in need thereof, comprising:
  a) administering to said patient a maintenance dose of about 5.0 mg of tirzepatide, or a pharmaceutically acceptable salt thereof, about once weekly for a minimum of about four weeks; and thereafter
  b) administering to said patient about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament to cure diabetes, induce remission or regression of diabetes, or prevent diabetes in a patient in need thereof, comprising:
  a) administering to said patient an escalation dose of about 7.5 mg of tirzepatide, or a pharmaceutically acceptable salt thereof, about once weekly for a minimum of about four weeks; and thereafter
  b) administering to said patient about 10.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament to cure diabetes, induce remission or regression of diabetes, or prevent diabetes in a patient in need thereof, comprising: administering to said patient a maintenance dose of about 10.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament to cure diabetes, induce remission or regression of diabetes, or prevent diabetes in a patient in need thereof, comprising:
  a) administering to said patient a maintenance dose of about 10.0 mg of tirzepatide, or a pharmaceutically acceptable salt thereof, about once weekly for a minimum of about four weeks; and thereafter
  b) administering to said patient about 15.0 mg of tirzepatide, or a pharmaceutically acceptable salt thereof, about once weekly for a minimum of about four weeks.

Another embodiment provides a use of tirzepatide, or a pharmaceutically acceptable salt thereof, in the manufacture of a medicament to cure diabetes, induce remission or regression of diabetes, or prevent diabetes in a patient in need thereof, comprising:
  a) administering to said patient an escalation dose of about 12.5 mg of tirzepatide, or a pharmaceutically acceptable salt thereof, about once weekly for a minimum of about four weeks; and thereafter
  b) administering to said patient about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament to cure diabetes, induce remission or regression of diabetes, or prevent diabetes in a patient in need thereof, comprising: administering to said patient a maintenance dose of about 15.0 mg of tirzepatide, or a pharmaceutically acceptable salt thereof, about once weekly for a minimum of about four weeks.

In another aspect, the present invention provides a use of tirzepatide, or a pharmaceutically acceptable salt thereof, in the manufacture of a medicament to cure diabetes, induce remission or regression of diabetes, or prevent diabetes in a patient in need thereof, comprising:
  a) administering to said patient an escalation dose of about 2.5 mg of tirzepatide, or a pharmaceutically acceptable salt thereof, about once weekly for a minimum of about four weeks; and thereafter
  b) administering to said patient a maintenance dose of about 5.0 mg of tirzepatide, or a pharmaceutically acceptable salt thereof, about once weekly for a minimum of about four weeks; and thereafter
  c) administering to said patient an escalation dose of about 7.5 mg of tirzepatide, or a pharmaceutically acceptable salt thereof, about once weekly for a minimum of about four weeks; and thereafter
  d) administering to said patient a maintenance dose of about 10.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose.

In another aspect, the present invention provides a use of tirzepatide, or a pharmaceutically acceptable salt thereof, in the manufacture of a medicament to cure diabetes, induce remission or regression of diabetes, or prevent diabetes in a patient in need thereof, comprising:
  a) administering to said patient an escalation dose of about 2.5 mg of tirzepatide, or a pharmaceutically acceptable salt thereof, about once weekly for a minimum of about four weeks; and thereafter
  b) administering to said patient a maintenance dose of about 5.0 mg of tirzepatide, or a pharmaceutically acceptable salt thereof, about once weekly for a minimum of about four weeks; and thereafter c) administering to said patient an escalation dose of about 7.5 mg of tirzepatide, or a pharmaceutically acceptable salt thereof, about once weekly for a minimum of about four weeks; and thereafter d) administering to said patient a maintenance dose of about 10.0 mg of tirzepatide, or a pharmaceutically acceptable salt thereof, about once weekly for a minimum of about four weeks; and thereafter e) administering to said patient an escalation dose of about 12.5 mg of tirzepatide, or a pharmaceutically acceptable salt thereof, about once weekly for a minimum of about four weeks; and thereafter f) administering to said patient a maintenance dose of about 15.0 mg of tirzepatide, or a pharmaceutically acceptable salt thereof, about once weekly for a minimum of about four weeks.

In another aspect, the present invention includes a medicament as described in the preceding paragraph but which does not include administering the 7.5 mg escalation dose. In another aspect, the present invention includes a medicament as described in the preceding paragraph but which does not include administering the 12.5 mg escalation dose. In another aspect, the present invention includes a medicament as described in the preceding paragraph but which does not include administering the 7.5 mg and 12.5 mg escalation doses.

An embodiment of the present invention for use in the manufacture of a medicament described above is wherein the escalation dose administered once weekly for four weeks is about 2.5 mg and the maintenance dose administered once weekly for four weeks is about 5.0 mg. A further embodiment of the present invention is wherein the escalation dose administered once weekly for four weeks is about 7.5 mg and the maintenance dose administered once weekly for four weeks is about 10.0 mg. A further embodiment of the present invention is wherein the escalation dose administered once weekly for four weeks is about 12.5 mg and the maintenance dose administered once weekly for four weeks is about 15.0 mg. A further embodiment of the present invention is wherein the escalation doses administered once weekly for four weeks are about 2.5 mg and about 7.5 mg and the maintenance doses administered once weekly for four weeks are about 5.0 mg and about 10.0 mg. A further embodiment of the present invention is wherein the escalation doses administered once weekly for four weeks are about 2.5 mg, about 5.0 mg and about 7.5 mg and the maintenance doses administered once weekly for four weeks are about 5.0 mg, about 10.0 mg and about 15.0 mg.

In embodiment 1a, is the use of tirzepatide, or a pharmaceutically acceptable salt thereof, in the manufacture of a medicament for preventing diabetes in a patient in need thereof, comprising: administering an escalation dose about once weekly for a minimum of about two weeks and thereafter administering maintenance dose about once weekly for a minimum of about two weeks; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof, and wherein the maintenance dose following an escalation dose is a 2.5 mg incremental increase relative to that escalation dose.

In embodiment 2a is the use of tirzepatide, or a pharmaceutically acceptable salt thereof, in the manufacture of a medicament for preventing diabetes in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof, and wherein the maintenance dose following an escalation dose is about a 5.0 mg incremental increase relative to that escalation dose.

In embodiment 3a, is the use of embodiment 1a or 2a, wherein the escalation dose is about 2.5 mg and the maintenance dose is about 5.0 mg.

In embodiment 4a, is the use of embodiment 1a or 2a, wherein the escalation dose is about 7.5 mg and the maintenance dose is about 10.0 mg.

In embodiment 5a, is the use of embodiment 1a or 2a, wherein the escalation dose is about 12.5 mg and the maintenance dose is about 15.0 mg.

In embodiment 6a, is the use of embodiment 3a, further comprising an escalation dose of about 7.5 mg and a maintenance dose of about 10.0 mg.

In embodiment 7a, is the use of embodiment 6a, further comprising an escalation dose of about 12.5 mg and a maintenance dose of a bout 15.0 mg. In embodiment 8a, is the use of tirzepatide, or a pharmaceutically acceptable salt thereof, in the manufacture of a medicament for treating chronic kidney disease in a patient in need thereof, comprising: administering an escalation dose about once weekly for a minimum of about two weeks and thereafter administering a maintenance dose about once weekly for a minimum of about two weeks; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof, and wherein the maintenance dose following an escalation dose is a 2.5 mg incremental increase relative to that escalation dose.

In embodiment 9a, is the use of tirzepatide, or a pharmaceutically acceptable salt thereof, in the manufacture of a medicament for treating chronic kidney disease in a patient in need thereof, comprising: administering at least one escalation dose about once weekly for a minimum of about four weeks and at least one maintenance dose about once weekly for a minimum of about four weeks following the escalation dose; wherein the escalation dose is selected from the group consisting of about 2.5 mg, about 7.5 mg and about 12.5 mg of tirzepatide, or a pharmaceutically acceptable salt thereof, wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is about a 5.0 mg incremental increase relative to that escalation dose.

In embodiment 10a is the use of embodiment 8a or 9a, wherein the escalation dose is about 2.5 mg and the maintenance dose is about 5.0 mg.

In embodiment 11a is the use of embodiment 8a or 9a, wherein the escalation dose is about 7.5 mg and the maintenance dose is about 10.0 mg.

In embodiment 12a is the use of embodiment 8a or 9a, wherein the escalation dose is about 12.5 mg and the maintenance dose is about 15.0 mg.

In embodiment 13a is the use of embodiment 10a, further comprising an escalation dose of about 7.5 mg and a maintenance dose of about 10.0 mg.

In embodiment 14a the use of embodiment 13a, further comprising an escalation dose of about 12.5 mg and a maintenance dose of about 15.0 mg.

In another aspect the present invention provides tirzepatide, or a pharmaceutically acceptable salt thereof, for use in treating type 2 diabetes. In an embodiment the present invention provides tirzepatide, or a pharmaceutically acceptable salt thereof, for use in treating type 2 diabetes in a patient in need thereof wherein: an escalation dose is administered about once weekly for a minimum of about four weeks and thereafter a maintenance dose is administered about once weekly for a minimum of about four weeks; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose. In another aspect the present invention provides tirzepatide, or a pharmaceutically acceptable salt thereof, for use in improving glycemic control. In another aspect the present invention provides tirzepatride, or a pharmaceutically acceptable salt thereof, for use in improving glycemic control in a patient in need thereof wherein: an escalation dose is administered about once weekly for a minimum of about four weeks and thereafter a maintenance dose is administered about once weekly for a minimum of about four weeks; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose. In another aspect the present invention provides tirzepatide, or a pharmaceutically acceptable salt thereof, for use in improving weight management. In another aspect the present invention provides tirzepatride, or a pharmaceutically acceptable salt thereof, for use in improving weight management in a patient in need thereof wherein: an escalation dose is administered about once weekly for a minimum of about four weeks and thereafter a maintenance dose is administered about once weekly for a minimum of about four weeks; wherein the escalation dose is selected from the group consisting of about 2.5 mg, about 7.5 mg and about 12.5 mg of tirzepatide, or a pharmaceutically acceptable salt thereof: wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose. In another aspect the present invention provides tirzepatide, or a pharmaceutically acceptable salt thereof, for use in treating chronic kidney disease. In another aspect the present invention provides tirzepatride, or a pharmaceutically acceptable salt thereof, for use in treating chronic kidney disease in a patient in need thereof wherein: an escalation dose is administered about once weekly for a minimum of about four weeks and thereafter a maintenance dose is administered about once weekly for a minimum of about four weeks; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof, and wherein the maintenance dose following an escalation dose is a 2.5 mg incremental increase relative to that escalation dose. In another aspect the present invention provides tirzepatide, or a pharmaceutically acceptable salt thereof, for use in treating atherosclerosis. In another aspect the present invention provides tirzepatride, or a pharmaceutically acceptable salt thereof, for use in treating atherosclerosis in a patient in need thereof wherein: an escalation dose is administered about once weekly for a minimum of about four weeks and thereafter a maintenance dose is administered about once weekly for a minimum of about four weeks; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose. In another aspect the present invention provides tirzepatide, or a pharmaceutically acceptable salt thereof, for use in treating NAFLD. In another aspect the present invention provides tirzepatride, or a pharmaceutically acceptable salt thereof, for use in treating NAFLD in a patient in need thereof wherein: an escalation dose is administered about once weekly for a minimum of about four weeks and thereafter a maintenance dose is administered about once weekly for a minimum of about four weeks; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose. In another aspect the present invention provides tirzepatide, or a pharmaceutically acceptable salt thereof, for use in treating NASH. In another aspect the present invention provides tirzepatide, or a pharmaceutically acceptable salt thereof, for use in treating NASH in a patient in need thereof wherein: an escalation dose is administered about once weekly for a minimum of about four weeks and thereafter a maintenance dose is administered about once weekly for a minimum of about four weeks; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose. In another aspect the present invention provides tirzepatide, or a pharmaceutically acceptable salt thereof, for use in curing diabetes, inducing remission or regression of diabetes, or preventing diabetes. In another aspect the present invention provides tirzepatride, or a pharmaceutically acceptable salt thereof, for use in curing diabetes, inducing remission or regression of diabetes, or preventing diabetes in a patient in need thereof wherein: an escalation dose is administered about once weekly for a minimum of about four weeks and thereafter a maintenance dose is administered about once weekly for a minimum of about four weeks; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg incremental increase relative to that escalation dose.

An embodiment of the present invention for the uses described above is wherein the escalation dose administered once weekly for four weeks is about 2.5 mg and the maintenance dose administered once weekly for four weeks is about 5.0 mg. A further embodiment of the present invention is wherein the escalation dose administered once weekly for four weeks is about 7.5 mg and the maintenance dose administered once weekly for four weeks is about 10.0 mg. A further embodiment of the present invention is wherein the escalation dose administered once weekly for four weeks is about 12.5 mg and the maintenance dose administered once weekly for four weeks is about 15.0 mg. A further embodiment of the present invention is wherein the escalation doses administered once weekly for four weeks are about 2.5 mg and about 7.5 mg and the maintenance doses administered once weekly for four weeks are about 5.0 mg and about 10.0 mg. A further embodiment of the present invention is wherein the escalation doses administered once weekly for four weeks are about 2.5 mg, about 5.0 mg and about 7.5 mg and the maintenance doses administered once weekly for four weeks are about 5.0 mg, about 10.0 mg and about 15.0 mg.

As used herein, "titration dose" or "escalation dose" means a dose that is less than the highest desired effective dose for the patient. As used herein, the invention contemplates that a "titration dose" or "escalation dose" may become the highest desired effective dose, or "maintenance dose" if such dose is observed to be the desired effective dose for the patient, and such dose may be administered chronically for a period exceeding four weeks.

As used herein "maintenance dose" means both a dose that is the highest desired effective dose for the patient, and the maintenance dose may become an escalation dose when such maintenance dose is less than the desired highest effective dose. That is to say, if, for a particular patient, the "about 5 mg" maintenance dose contemplated by the present invention is not the highest desired effective dose, then that 5 mg maintenance dose will become, in retrospect, a titration dose as the particular patient's dose will be increased up until reaching the next highest maintenance dose contemplated by the present invention, e.g., 7.5 mg for at least about 2 weeks to 10 mg for at least about 2 weeks. The invention contemplates that a patient that reaches a maintenance dose of about 10 mg or about 15 mg may, as determined by a physician or other health care provider, need to have their dosage decreased to a lower maintenance dose.

Also provided herein is tirzepatide for use in simultaneous, separate and sequential combinations with one or more agents selected from metformin, a thiazolidinedione, a sulfonylurea, a dipeptidyl peptidase 4 inhibitor, a sodium glucose co-transporter, a SGLT-2 inhibitor, a growth differentiation factor 15 modulator ("GDF15"), a peptide tyrosine tyrosine modulator ("PYY"), a modified insulin, amylin, a dual amylin calcitonin receptor agonist, and oxyntomodulin agonist ("OXM") in the treatment of a condition selected from the group consisting of type 2 diabetes, chronic kidney disease, atherosclerosis, NALFD and NASH. Further provided herein is a compound of the present invention for use in simultaneous, separate and sequential combinations with one or more agents selected from metformin, a thiazolidinedione, a sulfonylurea, a dipeptidyl peptidase 4 inhibitor, a sodium glucose co-transporter, a SGLT-2 inhibitor, GDF15, PYY, a modified insulin, amylin, a dual amylin calcitonin receptor agonist, and OXM in the improvement of glycemic control and/or weight management. Also provided herein is a compound of the present invention for use in simultaneous, separate and sequential combinations with one or more agents selected from metformin, a thiazolidinedione, a sulfonylurea, a dipeptidyl peptidase 4 inhibitor, a sodium glucose co-transporter, a SGLT-2 inhibitor, GDF15, PYY, a modified insulin, amylin, a dual amylin calcitonin receptor agonist, and OXM to cure diabetes, induce remission or regression of diabetes, or prevent diabetes. In an embodiment, a compound of the present invention is provided in a fixed dose combination with one or more agents selected from metformin, a thiazolidinedione, a sulfonylurea, a dipeptidyl peptidase 4 inhibitor, a sodium glucose co-transporter, a SGLT-2 inhibitor, GDF15, PYY, a modified insulin, amylin, a dual amylin calcitonin receptor agonist, and OXM.

NAFLD and NASH Treatments

Nonalcoholic fatty liver disease ("NAFLD") is a liver disease characterized by an accumulation of fat in the liver of afflicted patients. Patients suffering from NAFLD may consume little or no alcohol, and in an embodiment, the patient does not have comorbid diabetes. NAFLD is a major cause of liver disease worldwide. Younossi et. al. *Global epidemiology of nonalcoholic fatty liver disease-Meta-analytic assessment of prevalence, incidence, and outcomes*; Hepatology (July 2016) 64:1; 73-84. Nonalcoholic steatohepatitis ("NASH") is a type of NAFLD with an etiological constellation exhibiting macrovesicular hepatic steatosis, inflammation, hepatocyte ballooning, and fibrosis. NASH may lead to cirrhosis and liver failure. It has been established that patients with NASH are more likely to develop cirrhosis, and have a higher risk of cardiovascular mortality, and hepatocyte carcinoma. This non-alcoholic, non-viral cirrhosis is, in fact, among the top causes of liver transplantation.

NAFLD and NASH are progressive diseases characterized by the development of liver fibrosis as NAFLD progresses to NASH. The stage of NASH can be defined, for example, by the NASH CRN (Clinical Research Network). Fibrosis staging measures the amount and pattern of NASH fibrosis, as well as parenchymal architectural remodeling in a patient. NASH is typically diagnosed in a human patient using liver biopsy, and the diagnosis is predicted using MRI-derived proton density fat fraction images ("MRI-PDFF"), plasma cytokeratin 18 (CK18) fragment levels as a biomarker for hepatocyte apoptosis, and plasma Pro-C3 (N-terminal type III collagen propeptide) to predict fibrosis progression, and/or other biomarkers. Vincent Wai-Sun Wong, et. al. *Noninvasive biomarkers in NAFLD and NASH—current progress and future promise*; Nature Reviews Gastroenterology & Hepatology; (29 May 2018). NAFLD, in which excess lipid deposition occurs in the liver, is typically assessed using imaging methods such as MRI-PDFF.

Currently, there is no approved pharmaceutical medicament specifically for the treatment of NASH. Current NASH patient recommendations include diet and exercise. There is a need for pharmaceutical medicaments to offer additional treatment options for patients suffering from NAFLD and NASH.

The present invention provides a method for treating NAFLD, comprising administering an effective amount of tirzepatide or a pharmaceutically acceptable salt thereof, to a patient in need of such treatment. The present invention provides a method for treating NASH, comprising administering an effective amount of tirzepatide or a pharmaceutically acceptable salt thereof, to a patient in need of such treatment. In an embodiment, the patient in need of treatment for NASH has comorbid type 2 diabetes. In an embodiment, the patient in need of treatment for NASH does not have type 2 diabetes.

Chronic Kidney Disease Treatment

Chronic kidney disease ("CKD") is defined as abnormalities of kidney structure or function, present for three months, with implications for health of the patient. CKD can be classified on the basis of the glomular filtration rate ("GFR") into five categories. The GFR can be estimated using biomarkers, including serum creatinine and albumin, albumin to creatinine ratio ("ACR"), and serum cystatin C, Moderate CKD (GFR 30-59 mL/min/1.73 m2) is classified as stage 3 CKD. In the adult population, a decreasing GFR is associated with an increased cardiovascular disease ("CVD") risk, independent of other cardiovascular ("CV") risk factors. The CV mortality in patients with stage 3 and stage four CKD is two-fold and three-fold higher, respectively, when compared with patients with normal renal function. Patients with CKD and established CVD have a much higher mortality rate compared with patients with CVD and normal renal function. Therefore patients with CKD are considered high risk (stage 3 CKD) or very high risk (stage 4-5 CKD or on dialysis). Treatments for patients with CKD typically include diet, exercise, cessation of smoking, antihypertensive medications, and combinations of medications. Desired treatments for CKD reduce inflammation, improve glycemic control, and/or improve cellular function in such patients. There is a desire for additional treatment options for patients with CKD.

The present invention provides a method for treating CKD comprising administering an effective amount of tirzepatide to a patient in need thereof. In an embodiment, the treatment is for a patient with Stage 3 CKD. In an embodiment, the treatment is for a patient having Stage 4 CKD. In an embodiment, the treatment is for a patient having Stage 2 CKD. In an embodiment, the treatment is for a patient having Stage 1 CKD.

Atherosclerosis Treatment

Atherosclerosis is a condition that develops when plaque builds up in the walls of the arteries. This buildup narrows the arteries, impeding blood flow. Complications associated with atherosclerosis and the atherosclerosis disease progression may lead to a heart attack or stroke. Despite recent advancements in treatment options, cardiovascular disease remains the leading cause of death for people living with diabetes. The present invention provides a method for treating atherosclerosis comprising administering an effective amount of tirzepatide to a patient in need thereof.

Cure Diabetes, Induce Remission or Regression of Diabetes, or Prevent Diabetes

U.S. Pat. No. 9,474,780 teaches that tirzepatide is useful for the treatment of diabetes, wherein "treating" includes restraining, slowing, stopping, or reversing the progression or severity of an existing symptom or disorder. Despite advances in the treatment of diabetes, many patients receiving such treatment are unable to reach their glycemic control goal or HbA1c goal.

U.S. Pat. No. 9,474,780 teaches that tirzepatide is useful for the treatment of diabetes, wherein "treating" includes restraining, slowing, stopping, or reversing the progression or severity of an existing symptom or disorder. Despite advances in the treatment of diabetes, many patients receiving such treatment are unable to reach their glycemic control goal or HbA1c goal. This invention provides a cure for diabetes wherein a patient receiving treatment for diabetes using a tirzepatide dosing regimen comprising a 2.5 mg tirzepatide once weekly start dose or escalation dose is administered for four weeks and a 5.0 mg tirzepatide once weekly maintenance dose is administered for at least four weeks; if the patient does not achieve their HbA1c goal, then an escalation dose of about 7.5 mg once weekly is administered for at least four weeks and then a maintenance dose of 10.0 mg tirzepatide once weekly is administered for at least four weeks; wherein, if the patient does not achieve their HbA1c goal from at least 4 weeks treatment using the 10.0 mg once weekly dose, then a 12.5 mg tirzepatide once weekly escalation dose may be administered for at least 4 weeks, followed by a 15 mg once weekly maintenance dose administered until the HbA1c goal is achieved for at least about 2 weeks, and wherein such patient maintains their HbA1c goal after cessation of all medications approved for use in the treatment of diabetes or glycemic control. As used herein, the term "diabetes medication," "diabetes medicine" and the like, means a medication approved by the pertinent regulatory agency for use in the treatment of glycemic control or Type II diabetes. In an embodiment, the HbA1c measurement in the patient treated for diabetes is less than or equal to about 5.9%. In an embodiment, the patient maintains their HbA1c goal level for at least one month without further tirzepatide administration. In an embodiment, the patient previously treated for diabetes using tirzepatide maintains their glycemic goal for at least one month without administration of further tirzepatide or any other diabetes medication. In an embodiment, the patient maintains their glycemic goal for at least 6 months without administration of further tirzepatide or any other diabetes medication.

As used herein, the term "diabetes medication," "diabetes medicine" and the like, means a medication approved by the pertinent regulatory agency for use in the treatment of glycemic control or Type II diabetes. In an embodiment, the HbA1c measurement in the patient treated for diabetes is less than or equal to about 5.9%. In an embodiment, the patient maintains their HbA1c goal level for at least one month without further tirzepatide administration. In an embodiment, the patient previously treated for diabetes using tirzepatide maintains their glycemic goal for at least one month without administration of further tirzepatide or any other diabetes medication. In an embodiment, the patient maintains their glycemic goal for at least 6 months without administration of further tirzepatide or any other diabetes medication.

The doses of the present invention are likely to have specific concentrations of 5 mg/mL, 10 mg/mL, 15 mg/mL, 20 mg/mL, 25 mg/mL and 30 mg/mL. Such compositions may be presented in a pre-filled syringe. Such pre-filled syringe may be useful for administering one half milliliter of such composition per patient per dose. The doses of the present invention are typically administered subcutaneously. The doses are typically administered using a pre-filled, disposable pen, reusable pen, or automatic pen injector. In an embodiment, the device is an automatic injection apparatus as claimed by U.S. Pat. No. 8,734,394.

As used herein, "tirzepatide" means a GIP/GLP1 dual agonist peptide as described in U.S. Pat. No. 9,474,780 and described by CAS Registry Number: 2023788-19-2. Tirzepatide is described in Example 1 of U.S. Pat. No. 9,474,780, with the following sequence: YX$_1$EGTFTSDYSIX$_2$LDKIAQKAFVQWLIAGGPSSGAPPPS wherein X$_1$ is Aib; X$_2$ is Aib; K at position 20 is chemically modified through conjugation to the epsilon-amino group of the K side-chain with (2-[2-(2-Amino-ethoxy)-ethoxy]-acetyl)$_2$-(γGlu)$_1$-CO—(CH$_2$)$_{18}$—CO$_2$H; and the C-terminal amino acid is amidated as a C-terminal primary amide (SEQ ID NO: 1).

As used herein, the term "administering" means the administration by a nurse, health care provider, patient or any other individual including self-administration. This includes not only delivering into the body but also prescribing, dispensing or assisting in any way with delivery.

As used herein, the term "increasing the dose", "increasing the maintenance dose", "increasing the titration dose" and "increasing the escalation dose" means the raising of the respective dose by a nurse, health care provider, patient or any other individual.

As used herein, "pharmaceutically acceptable salt" is well known to the skilled artisan. In an embodiment is a pharmaceutically acceptable salt that is a tirzepatide trifluoroacetate salt. In an embodiment is tirzepatide as a non-salt.

As used herein, the term "biomarker", means a laboratory measurement that reflects the activity of a disease process. Biomarkers may be used to diagnose a disease or condition, and usually quantitatively correlate (either directly or inversely) with disease progression. In the clinical trial setting, a biomarker is a measure of the effect of a specific treatment that may correlate with an actual clinical endpoint but does not necessarily have a precise relationship; that is, a biomarker is a substitute measure for a clinical endpoint.

As used herein, the terms "treatment," "treat," "treating," and the like, mean to include slowing or attenuating the progression of a disease or disorder. The terms include to alleviate, ameliorate, or reduce one or more symptoms of a disorder or condition, even if the disorder or condition is not eliminated or if the progression is not slowed.

As used herein "cure diabetes" means that a patient, using tirzepatide for the treatment of diabetes reaches their glycemic control treatment goal. The tirzepatide treatment to cure diabetes can prevent, reduce the severity of, or induce remission of diabetes in such patient. In an embodiment, tirzepatide treatment slows the progression of diabetes in a patient in need of such treatment. In an embodiment, a patient using tirzepatide for treatment of diabetes, reaches their glycemic control treatment goal, and requires no concomitant diabetes medicine to maintain the glycemic control goal. In an embodiment, a patient using tirzepatide in the treatment of diabetes reaches at least their glycemic control treatment goal, and the treatment goal is maintained with cessation of treatment using tirzepatide and all other diabetes medication. In an embodiment, a patient using tirzepatide in the treatment of diabetes reaches at least their glycemic control treatment goal, and the treatment goal is maintained for at least a about a month with cessation of treatment using tirzepatide and all other diabetes medications. In an embodiment, a patient using tirzepatide in the treatment of diabetes reaches at least their glycemic control treatment goal, and the treatment goal is maintained for at least about six months with cessation of treatment using tirzepatide and all other diabetes medications. In an embodiment the patient is unable to reach their glycemic goals prior to tirzepatide treatment. In an embodiment, the patient has failed to reach their glycemic goal using oral diabetes medication. In an embodiment, the patient has failed to reach their glycemic goal using metformin treatment. In an embodiment, the patient glycemic goal is less than about 5.9% HbA1c.

As used herein "glycemic control" refers to the maintenance or reduction of a patient's HbA1c levels; "improving" glycemic control refers to reductions in HbA1c.

As used herein "weight management" refers to the management of obesity in an individual; "improving" weight management refers to a reduction in body weight.

As used herein "HbA1c" refers to glycated hemoglobin levels, which develop when hemoglobin joins with glucose in the blood. HbA1c levels are a commonly used measure of glycemic control in patients with diabetes, with decreased HbA1c levels generally indicating improved glycemic control. In the context of the methods of the present invention, the methods of the present invention result in a decrease in HbA1c. In certain embodiments, the decrease in HbA1c is decreased relative to the HbA1c levels resulting from treatment with a lower dose of tirzepatide.

As used herein "patient" or "patients" refers to a mammal in need of treatment for a condition or disorder. In an embodiment, the patient is a human with a disease or condition that would benefit from treatment with tirzepatide.

The term "LOCF" or last observation carried forward are recognized by the skilled statistician as a statistical analysis method that imputes missing data. The term "ITT" or intention to treat are recognized by the skilled statistician as the intention to treat analysis method wherein participants are analyzed according to the group they were originally assigned.

Preparation #1—Tirzepatide Composition Containing NaCl

The composition is prepared substantially as described herein. The compositions containing 5, 10, 15, 20, 15, and 30 mg/mL of tirzepatide each contain the ingredients set forth in Table 1. Acid or base is optionally added to attain the desired pH range. Water is added quantum satis (q.s.) to one milliliter total final volume.

TABLE 1

Formulation of tirzepatide, Phosphate, and NaCl

| Ingredient | Concentration (mg/mL) |
| --- | --- |
| Tirzepatide | 5, 10, 15, 20, 25, and 30 |
| dibasic sodium phosphate* | 1.34 |
| NaCl | 8.2 |

*5 mM phosphate buffer is used

Preparation #2—Tirzepatide Composition Containing Propylene Glycol

The composition is prepared substantially as described herein. The compositions providing 5, 10, 15, 20, 15, and 30 mg/mL compositions of tirzepatide each contain the ingredients set forth in Table 2. Acid or base is optionally added to attain the desired pH range. Water is added quantum satis to one milliliter total final volume.

TABLE 2

Formulation of tirzepatide, Phosphate, and Propylene Glycol

| Ingredient | Concentration (mg/mL) |
|---|---|
| Tirzepatide | 5, 10, 15, 20, 25, and 30 |
| dibasic sodium phosphate* | 1.34 |
| Propylene glycol | 15 |

*5 mM phosphate buffer is used

Clinical Study (NCT03131687) Supporting Maintenance Dose Embodiments

A 6-month (26-week) Phase 2 double-blind clinical study is designed to evaluate the safety, efficacy, and PK/PD of 4 dose levels (1 mg, 5 mg, 10 mg and 15 mg respectively) of tirzepatide once weekly by subcutaneous injection compared with dulaglutide 1.5 mg. once weekly (QW) and placebo QW in patients with T2DM who have inadequate glycemic control with diet and exercise with or without a stable dose of metformin. Tirzepatide dose is up-titrated to the maintenance dose using the following weekly dose increments:

| Tirzepatide dose: | Weekly Tirzepatide Dose Increments: |
|---|---|
| 1 mg (LY 1 mg) | Week 0-26: 1 mg QW |
| 5 mg (LY 5 mg) | Week 0-26: 5 mg QW |
| 10 mg (LY10 mg) | Week 0: 5 mg |
| | Week 1: 5 mg |
| | Week 2-26: 10 mg |
| 15 mg (LY15 mg) | Week 0: 5 mg |
| | Week 1: 5 mg |
| | Week 2: 10 mg |
| | Week 3: 10 mg |
| | Week 4: 10 mg |
| | Week 5: 10 mg |
| | Week 6-26: 15 mg |

The study also has a 4-week follow up period. In addition to safety and efficacy for treating T2DM, efficacy endpoints include the effect of tirzepatide on HbA1c, FBG, body weight, lipids, and waist circumference compared with placebo and with dulaglutide 1.5 mg. The study also evaluates the effect of tirzepatide on GI tolerability, hypoglycemia, hypersensitivity reactions, and pancreatic safety, as well as the development of treatment-emergent anti-drug antibodies. Model-based dose response analyses are performed to predict potential for significant HbA1c lowering and weight loss in longer studies.

Statistical Analyses:

Efficacy: The primary efficacy outcome of HbA1c change from baseline to the 26-week endpoint is analyzed using a Bayesian dose-response model. Analyses are performed on the intention to treat population (mITT) analysis set. Supportive analysis of the primary efficacy outcome for the mITT dataset are the model for post-baseline measures (MMRM) with body mass index (BMI) ($<30$ kg/m$^2$, $\geq 30$ kg/m$^2$), metformin use, treatment, visit, and treatment-by-visit interaction as fixed effects, baseline HbA1c as a covariate, and patient as a random effect.

The mean weight change from baseline at 12 and 26 weeks, along with the mean change from baseline of HbA1c at 12 weeks, is analyzed using similar dose-response models as the primary analyses. The percentages of patients with $\geq 5\%$ or $\geq 10\%$ body weight loss, reaching the HbA1c target of $\leq 6.5\%$ or $\leq 7.0\%$ at 26 weeks, or requiring rescue therapy are analyzed using logistic regression with fixed effects of treatment and strata, and baseline as a covariate. The changes from baseline in FBG (fasting blood glucose), SMBG (self-monitored blood glucose) levels, waist circumference, and mean percentage change in lipids from baseline to 12 and 26 weeks are analyzed using a similar MMRM to the one used for the primary analyses.

Table Abbreviations: Dula 1.5 mg=dulaglutide 1.5 mg once weekly; LY means tirzepatide, and LY 1 mg=tirzepatide 1 mg once weekly; LY 5 mg=5 mg once weekly; LY 10 mg=escalation dose group tirzepatide once weekly with highest dose of 10 mg; LY 15 mg=escalation dose group of tirzepatide once weekly with highest dose 15 mg; LOCF=last observation-carried-forward; N=number of patients; pbo=placebo; Week 26=mITT on-treatment data at Week 26 excluding data after study drug discontinuation or rescue drug initiation; mITT=modified intent-to-treat; SD=standard deviation. For Table 4, n=number of patients in the population with baseline and post-baseline value at the specified time point. For Table 6, LY10 mg=escalation dose group tirzepatide, once weekly with highest dose of 10 mg; escalation dose: (5 mg weeks 0 and 1), LY15 mg=escalation dose group tirzepatide, once weekly with highest dose of 15 mg; escalation dose: (5 mg weeks 0 and 1; 10 mg weeks 2 to 5); N=number of patients in specified group, m=number of patients who experienced new event during interval, FolUp=follow up, T/Wk=Time range, (week) and %=means percent patients spending at least some time in treatment group who experienced new event during interval. For Table 7, n is the number of patients with events meeting the criteria; N is number of patients in the population; % is percent of patients in treatment group experiencing the event.

TABLE 3

HbA1c Data

| | Endpoint | % of Patients Reaching HbA1c Target <6% (odds ratio vs. placebo) | p-value (vs. pbo) | % of Patients Reaching HbA1c Target <5.7% (odds ratio vs. placebo) | p-value (vs. pbo) |
|---|---|---|---|---|---|
| Placebo | LOCF Week 26 (N = 51) | 2.0% (-) | — | 2.0% (-) | — |
| | mITT Week 26 (N = 41) | 2.4% (-) | — | 2.4% (-) | — |
| LY 5 mg | LOCF Week 26 (N = 55) | 25.5% (11.8) | p = 0.005 | 3.6% (1.6) | p = 0.651 |
| | mITT Week 26 (N = 48) | 23.4% (10.5) | p = 0.010 | 4.3% (1.7) | p = 0.635 |
| LY 10 mg | LOCF Week 26 (N = 51) | 46.0% (28.7) | p < 0.001 | 18.0% (7.8) | p = 0.022 |
| | mITT Week 26 (N = 44) | 51.2% (34.5) | p < 0.001 | 20.9% (7.9) | p = 0.025 |
| LY 15 mg | LOCF Week 26 (N = 53) | 37.7% (22.0) | p < 0.001 | 30.2% (14.4) | p = 0.002 |
| | mITT Week 26 (N = 35) | 54.3% (48.7) | p < 0.001 | 42.9% (26.6) | p < 0.001 |
| Dula 1.5 mg | LOCF Week 26 (N = 54) | 11.1% (4.5) | p = 0.107 | 1.9% (1.0) | p = 0.969 |

TABLE 3-continued

HbA1c Data

| Endpoint | % of Patients Reaching HbA1c Target <6% (odds ratio vs. placebo) | p-value (vs. pbo) | % of Patients Reaching HbA1c Target <5.7% (odds ratio vs. placebo) | p-value (vs. pbo) |
| --- | --- | --- | --- | --- |
| mITT Week 26 (N = 47) | 12.8% (4.5) | p = 0.116 | 2.1% (0.89) | p = 0.922 |

Data in Table 3 support that 5 mg, 10 mg, and 15 mg doses of tirzepatide significantly decrease HbA1c from baseline and are significantly different from placebo. The artisan will appreciate that HbA1c values of less than 5.7% are consistent with levels observed in a patient without diabetes. The tirzepatide dose groups are also significantly different from dulaglutide 1.5 mg.

The percentage of patients reaching HbA1c treatment goals in Table 3 show that more patients in the tirzepatide 15-mg group who stay on study drug are able to reach a treatment goal of HbA1c≤5.7% than any other treatment group.

TABLE 4

Mean Fasting Glucose Value

| Week 26/ Treatment | N | Mean glucose value (mg/dl) | SD | Mean change from baseline | SD |
| --- | --- | --- | --- | --- | --- |
| Placebo | 40 | 171.1 | 46.59 | 16.7 | 31.35 |
| LY1 mg | 44 | 154.9 | 49.36 | −6.2 | 55.25 |
| LY5 mg | 48 | 126.5 | 33.11 | −46.7 | 48.32 |
| LY10 mg | 44 | 104.8 | 18.65 | −66.9 | 49.06 |
| LY15 mg | 35 | 110.3 | 32.13 | −56.8 | 67.29 |
| Dula 1.5 mg | 46 | 140.5 | 52.69 | −34.9 | 68.35 |

As expected from observed changes in HbA1c, the tirzepatide 5 mg, 10 mg, and 15 mg doses significantly decrease fasting serum glucose compared with placebo and dulaglutide 1.5 mg as shown in Table 4.

TABLE 5

Weight Loss

| Treatment | % of Patients Achieving Weight loss ≥10% (odds ratio vs. placebo | p-value (vs. pbo) | % of Patients Achieving Weight loss ≥15% (odds ratio vs. placebo |
| --- | --- | --- | --- |
| Placebo | 0 (-) | — | — |
|  | 0 (-) | — | 0 |
| LY 1 mg | LOCF 5.8% (7.1) | p = 0.193 | — |
|  | 6.8% (6.7) | p = 0.218 | 0 |
| LY 5 mg | LOCF 16.4% (20.8) | p = 0.036 | — |
|  | 16.7% (17.2) | p = 0.056 | 6.3% |
| LY 10 mg | LOCF 39.2% (67.6) | p = 0.003 | — |
|  | 45.5% (71.7) | p = 0.004 | 25.0% |
| LY 15 mg | LOCF 37.7% (66.2) | p = 0.003 | — |
|  | 54.3% (109.2) | p = 0.001 | 34.3% |
| Dula 1.5 mg | LOCF 9.3% (11.7) | p = 0.095 | — |
|  | 10.6% (10.4) | p = 0.121 | 2.1% |

Table 5 summarizes the proportion of patients who attained a weight loss target of ≥5%, ≥10%, and ≥15% at Week 26. The 5 mg, 10 mg, and 15 mg doses of tirzepatide significantly decrease body weight from baseline and are significantly different from placebo. The tirzepatide 5 mg, 10 mg, and 15 mg groups are also significantly different from dulaglutide 1.5 mg As shown by Table 5 summarizing a clinical study, a larger percentage of patients in the tirzepatide 15 mg group were able to reach a mean body weight reduction of over 15%.

TABLE 6

Nausea Vomiting and Diarrhea

| T/Wk | Placebo N = 51 | LY10 mg N = 51 | LY15 mg N = 53 | Dula 1.5 mg N = 54 |
| --- | --- | --- | --- | --- |
| 0 | m = 0; 0% | m = 9; 20% | m = 17; 32.1% | m = 12; 22.2% |
| 1 | m = 1; 2% | m = 2; 3.9% | m = 10; 18.9% | m = 2; 3.7% |
| 2 | m = 0; 0% | m = 2; 3.9% | m = 3; 5.8% | m = 0; 0.0% |
| 3 | m = 0; 0% | m = 1; 2.0% | m = 6; 11.4% | m = 2; 3.8% |
| 4 | m = 0; 0% | m = 3; 6.0% | m = 3; 5.9% | m = 1; 1.9% |
| 5 | m = 0; 0% | m = 2; 4.0% | m = 1; 2.0% | m = 0; 0.0% |
| 6 | m = 0; 0% | m = 1; 2.0% | m = 2; 3.9% | m = 0; 0.0% |
| 7 | m = 1; 2% | m = 2; 4.1% | m = 3; 5.9% | m = 1; 1.9% |
| 8 | m = 0; 0% | m = 1; 2.0% | m = 2; 4.0% | m = 0; 0.0% |
| 9 | m = 0; 0% | m = 2; 4.1% | m = 0; 0.0% | m = 1; 1.9% |
| 10 | m = 0; 0% | m = 0; 0% | m = 0; 0.0% | m = 0; 0.0% |
| 11 | m = 0; 0% | m = 0; 0% | m = 1; 2.0% | m = 0; 0.0% |
| 12 | m = 0; 0% | m = 1; 2.0% | m = 1; 2.1% | m = 1; 2.0% |
| >12 < 16 | m = 1; 2% | m = 1; 2.0% | m = 1; 2.1% | m = 2; 3.9% |
| >16 ≤ 20 | m = 0; 0% | m = 1; 2.1% | m = 1; 2.1% | m = 1; 2.0% |
| >20 | m = 1; 2.1% | m = 1; 2.1% | m = 1; 2.1% | m = 4; 7.8% |
| Fol Up | m = 0; 0% | m = 1; 2.1% | m = 0; 0.0% | m = 3; 5.9% |

Table 6 illustrates the advantageous effect on gastrointestinal adverse event incidence using the methods herein.

TABLE 7

Decrease Appetite

| Event | Placebo N = 51 | LY1 mg N = 52 | LY5 mg N = 55 | LY10 mg N = 51 | LY15 mg N = 53 | Dula 1.5 mg N = 54 |
| --- | --- | --- | --- | --- | --- | --- |
| Decrease Appetite (reported) | n = 1; 2.0% | n = 2; 3.8% | n = 10; 18.2% | n = 13; 25.5% | n = 10; 18.9% | n = 3; 5.6% |

Decrease in appetite is a centrally mediated effect. The data presented in Table 7 are reported from a clinical trial, suggesting that tirzepatide has some centrally mediated effects. The centrally mediated activity of tirzepatide may provide additional treatment options for patients seeking a treatment to provide centrally mediated GIP/GLP1 agonist activity.

In NCT03131687, the 15 mg dose was associated with higher GI AEs and higher frequency of patients discontinuing study treatment early after relatively short escalation. A 15 mg dose with a more acceptable tolerability profile is desired. Data from NCT03131687, support 15 mg dose as the highest clinically relevant maintenance dose as contemplated by the present invention. Escalation schemes, as claimed herein were investigated to facilitate an acceptably tolerable 15 mg maintenance dosage. See Clinical Study (NCT03311724) immediately below.

Clinical Study (NCT03311724) Supporting 2.5 Escalation Increments

This is a 12-week treatment with a 1 week screening (Visit 1) followed by a 1 week lead-in (Visit 2), then 12 weeks of treatment (Visits 3-10, including telephone visits), then followed by 4-week safety follow-up. It is a Phase 2 study designed to examine the efficacy and tolerability of subcutaneously once-weekly tirzepatide compared with placebo in patients with type 2 diabetes who have inadequate glycemic control with diet and exercise alone or with a stable dose of metformin. The study was designed per below and conducted to refine the escalation scheme.

| Tirzepatide dose Group: | Weekly Tirzepatide Dose Increments: |
|---|---|
| Placebo | Week 1-12 |
| Group 1 | Weeks 1-2: 2.5 mg |
|  | Weeks 3-4: 5 mg |
|  | Weeks 5-8: 10 mg |
|  | Weeks 9-12: 15 mg |
| Group 2 | Weeks 1-4: 2.5 mg |
|  | Weeks 5-8: 7.5 mg |
|  | Weeks 9-12: 15 mg |
| Group 3 | Weeks 1-4: 4 mg |
|  | Weeks: 5-8: 8 mg |
|  | Weeks 9-12: 12 mg |

TABLE 8

HbA1c Data at Week 12-mITT Population with On Treatment Dataset

|  | Endpoint | % of Patients Reaching HbA1c Target <7% (odds ratio vs. placebo) | p-value (vs. pbo) | % of Patients Reaching HbA1c Target <5.7% (odds ratio vs. placebo) | p-value (vs. pbo) |
|---|---|---|---|---|---|
| Placebo | LOCF Week 12 (N = 24) | 12.5 (-) | — | 0 (-) | — |
|  | Week 12 (N = 20) | 10.0 (-) | — | 0 (-) | — |
| LY 12 mg Group 3 | LOCF Week 12 (N = 28) | 71.4 (16.1) | p < 0.001 | 3.6 (2.8) | p = 0.509 |
|  | Week 12 (N = 27) | 74.1 (56.5) | p < 0.001 | 3.7 (2.5) | p = 0.568 |
| LY 15 mg-Group 1 | LOCF Week 12 (N = 28) | 78.6 (25.1) | p < 0.001 | 3.6 (2.9) | p = 0.494 |
|  | Week 12 (N = 23) | 87.0 (183.5) | p < 0.001 | 4.3 (3.1) | p = 0.482 |
| LY 15 mg-Group 2 | LOCF Week 12 (N = 27) | 85.2 (37.9) | p < 0.001 | 7.4 (5.0) | p = 0.270 |
|  | Week 12 (N = 26) | 84.6 (157.5) | p < 0.001 | 7.7 (4.6) | p = 0.321 |

LOCF = last-observation-carried-forward;
LY = tirzepatide;
mITT = modified intent-to-treat;
N = number of patietns;
pbo = placebo;
Week 12: mITT on-treatment at Week 12, excluding data after study drug discontinuation or rescue drug initiation;
LOCF Week 12: mITT on-treatment, excluding data after study drug discontinuation or rescue drug inhibition, last-observation-carried-forward to Week 12.

As shown by Table 8, after 12 weeks of treatment, including an 8-week escalation period, placebo-adjusted changes from baseline in HbA1c with 12-mg and 15-mg tirzepatide doses were statistically significant and clinically relevant.

TABLE 9

Weight Loss Data at Week 12-mITT Population with On Treatment Dataset

|  | Endpoint | % of Patients Achieving Weight loss ≥5% (odds ratio vs. placebo | p-value (vs. pbo) | % of Patients Achieving Weight loss ≥10% (odds ratio vs. placebo) | p-value (vs. pbo) |
|---|---|---|---|---|---|
| Placebo | LOCF Week 12 (N = 23) | 4.3 (-) | — | 0 (-) | — |
|  | Week 12 (N = 20) | 5.0 (-) | — | 0 (-) | — |
| LY 12 mg Group 3 | LOCF Week 12 (N = 27) | 63.0 (22.7) | p < 0.001 | 18.5 (10.4) | p = 0.101 |
|  | Week 12 (N = 27) | 63.0 (20.7) | p = 0.001 | 18.5 (9.3) | p = 0.129 |
| LY 15 mg-Group 1 | LOCF Week 12 (N = 27) | 59.3 (20.5) | p = 0.001 | 14.8 (8.0) | p = 0.150 |
|  | Week 12 (N = 23) | 56.5 (17.1) | p = 0.003 | 13.0 (6.2) | p = 0.225 |
| LY 15 mg-Group 2 | LOCF Week 12 (N = 27) | 55.6 (17.6) | p = 0.002 | 18.5 (10.6) | p = 0.099 |
|  | Week 12 (N = 26) | 57.7 (17.4) | p = 0.003 | 19.2 (9.7) | p = 0.121 |

LOCF = last-observation-carried-forward;
LY = tirzepatide;
mITT = modified intent-to-treat;
N = number of patietns;
pbo = placebo;
Week 12: mITT on-treatment at Week 12, excluding data after study drug discontinuation or rescue drug initiation;
LOCF Week 12: mITT on-treatment, excluding data after study drug discontinuation or rescue drug inhibition, last-observation-carried-forward to Week 12.

As shown by Table 9, both doses tirzepatide doses had significant reductions in body weight compared with placebo at 12 weeks.

TABLE 10

Nausea Vomiting and Diarrhea

| T/Wk | Placebo N = 26 | LY12 mg Group 3 N = 29 | LY15 mg-Group 1 N = 28 | LY15 mg-Group 2 N = 28 |
|---|---|---|---|---|
| 0 | m = 3; M = 26 | m = 9; M = 29 | m = 6; M = 28 | m = 4; M = 28 |
| 1 | m = 1; M = 26 | m = 5; M = 29 | m = 3; M = 28 | m = 4; M = 28 |
| 2 | m = 0; M = 25 | m = 1; M = 29 | m = 2; M = 28 | m = 2; M = 28 |
| 3 | m = 0; M = 25 | m = 3; M = 29 | m = 1; M = 27 | m = 3; M = 28 |
| 4 | m = 0; M = 25 | m = 3; M = 29 | m = 5; M = 27 | m = 6; M = 28 |
| 5 | m = 0; M = 24 | m = 0; M = 29 | m = 6; M = 27 | m = 2; M = 28 |
| 6 | m = 0; M = 24 | m = 2; M = 29 | m = 2; M = 27 | m = 3; M = 28 |
| 7 | m = 0; M = 24 | m = 1; M = 29 | m = 0; M = 27 | m = 2; M = 27 |
| 8 | m = 1; M = 24 | m = 4; M = 29 | m = 4; M = 27 | m = 5; M = 27 |
| 9 | m = 0; M = 24 | m = 1; M = 29 | m = 0; M = 27 | m = 2; M = 27 |
| 10 | m = 0; M = 24 | m = 1; M = 29 | m = 3; M = 27 | m = 0; M = 27 |
| 11 | m = 0; M = 24 | m = 0; M = 29 | m = 2; M = 27 | m = 3; M = 27 |
| 12 | m = 0; M = 23 | m = 1; M = 29 | m = 0; M = 27 | m = 0; M = 27 |

TABLE 10-continued

Nausea Vomiting and Diarrhea

| T/Wk | Placebo N = 26 | LY12 mg Group 3 N = 29 | LY15 mg-Group 1 N = 28 | LY15 mg-Group 2 N = 28 |
|---|---|---|---|---|
| Follow-up | m = 0; M = 23 | m = 1; M = 29 | m = 0; M = 27 | m = 0; M = 27 |
| Overall | m = 3; M = 26 | m = 14; M = 26 | m = 16; M = 28 | m = 13; M = 28 |

LY 12 mg Group 3, above = escalation dose group of tirzepatide once weekly with sequence of 4 mg × 4, 8 mg × 4, 12 mg × 4
LY 15 mg-Grou 1, above = escalation dose group of tirzepatide once weekly with sequenc of 2.5 mg × 2, 5 mg × 2, 10 mg × 4, 15 mg × 4
LY 15 mg-Group 2, above = escalation dose group of tirzepatide once weekly with sequence of 2.5 mg × 4, 7.5 mg × 4, 15 mg × 4
M = number of patients who had at least some time in interval
m = number of patients who experienced new event during interval where newly occurred event means that a patient has a new onset of an event during that period
N = numer of patients in specified treatment group As shown by Table 10, the most common adverse events were gastrointestinal events, including nausea, vomiting and diarrhea. Most of these vents were mild to moderate. No patient discontinued the study due to gastrointestinal tolerability adverse events or any other adverse vents.

Based on these data above from NCT03311724 an escalation scheme using 2.5 mg dose increments per 4 weeks is further supported.

Biomarkers

Clinically relevant biomarkers are measured in clinical studies to further support the use of tirzepatide for treating chronic kidney disease. In study NCT03131687, no decrease in eGFR was observed at any dosage. Clinical study laboratory measurements support the use of tirzepatide in the treatment of chronic kidney disease. Clinically relevant biomarkers are measured to assess and support the use of tirzepatide in the treatment of atherosclerosis. Clinically relevant triglyceride levels decrease in all tirzepatide treatment groups. Clinical observations support that tirzepatide can be beneficial for use in the treatment of atherosclerosis.

Biomarkers predictive of NAFLD are observed during clinical studies to demonstrate the beneficial effect of tirzepatide in the treatment of NAFLD. Biomarkers predictive of NASH are observed during clinical studies to demonstrate the beneficial effect of tirzepatide in the treatment of NAFLD. HbA1c levels in tirzepatide treated patients reaching their glycemic control goals, and ceasing the use of diabetes medications, are measured during follow up to validate a diabetes cure in such patients.

EXAMPLE 1

Clinical Dosing Regimen

A clinical trial studying the three maintenance doses of the present invention (5.0 mg, 10.0 mg and 15.0 mg) in the dosing regimens of the present invention is conducted as follows.

The starting dose of tirzepatide is 2.5 mg once weekly for 4 weeks, followed by an increase to 5 mg once weekly, for the duration of the study low-dose arm.

For the 10-mg arm, the starting dose of tirzepatide is 2.5 mg once weekly for 4 weeks, then the dose is increased by 2.5 mg every 4 weeks (5 mg once weekly for 4 weeks then 7.5 once weekly for four weeks) until the 10-mg dose is reached and maintained for the duration of the study.

For the 15-mg arm, the starting dose of tirzepatide will be 2.5 mg once weekly for 4 weeks, then the dose will be increased by 2.5 mg every 4 weeks (5 mg once weekly for four weeks then 7.5 mg once weekly for four weeks then 10 mg once weekly for four weeks then 12.5 mg once weekly for four weeks) until the 15-mg tirzepatide dose is reached and maintained for the duration of the study. For patients who cannot tolerate the 15 mg dose, the maintenance dose may be decreased to 10 mg.

Sequences

SEQ ID NO:1

Tirzepatide

YX$_1$EGTFTSDYSIX$_2$LDKIAQKAFVQWLIAGGPSSGAPPPS wherein X$_1$ is Aib; X$_2$ is Aib; K at position 20 is chemically modified through conjugation to the epsilon-amino group of the K side-chain with (2-[2-(2-Amino-ethoxy)-ethoxy]-acetyl)$_2$-(γGlu)$_1$-CO—(CH$_2$)$_{18}$—CO$_2$H; and the C-terminal amino acid is amidated as a C-terminal primary amide

We claim:

1. A method of treating type 2 diabetes in a patient in need thereof, comprising: administering an escalation dose about once weekly for a minimum of at least about two weeks and thereafter administering a maintenance dose about once weekly for a minimum of at least about two weeks; wherein the escalation dose is selected from the group consisting of about 2.5 mg, about 7.5 mg and about 12.5 mg of tirzepatide, or a pharmaceutically acceptable salt thereof; and wherein the maintenance dose is selected from the group consisting of about 5.0 mg, about 10.0 mg and about 15.0 mg of tirzepatide, or a pharmaceutically acceptable salt thereof.

2. The method of claim 1 for treating type 2 diabetes in a patient in need thereof, comprising: administering at least one escalation dose about once weekly for a minimum of about four weeks and at least one maintenance dose about once weekly for a minimum of about four weeks following the escalation dose; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg increment.

3. The method of claim 2, wherein the escalation dose is about 2.5 mg and the maintenance dose is about 5.0 mg.

4. The method of claim 2, wherein the escalation dose is about 7.5 mg and the maintenance dose is about 10.0 mg.

5. The method of claim 2, wherein the escalation dose is about 12.5 mg and the maintenance dose is about 15.0 mg.

6. A method of improving glycemic control in a patient in need thereof, comprising: administering an escalation dose about once weekly for a minimum of at least about two weeks and thereafter administering a maintenance dose about once weekly for a minimum of at least about two weeks; wherein the escalation dose is selected from the group consisting of about 2.5 mg, about 7.5 mg and about 12.5 mg of tirzepatide, or a pharmaceutically acceptable salt thereof; and wherein the maintenance dose is selected from the group consisting of about 5.0 mg, about 10.0 mg and about 15.0 mg of tirzepatide, or a pharmaceutically acceptable salt thereof.

7. The method of claim 6 of improving glycemic control in a patient in need thereof, comprising: administering an escalation dose about once weekly for a minimum of about four weeks and thereafter administering a maintenance dose about once weekly for a minimum of about four weeks; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is about a 2.5 mg incremental increase relative to that escalation dose.

8. The method of claim 7, wherein the escalation dose is about 2.5 mg and the maintenance dose is about 5.0 mg.

9. The method of claim 7, wherein the escalation dose is about 7.5 mg and the maintenance dose is about 10.0 mg.

10. The method of claim 7, wherein the escalation dose is about 12.5 mg and the maintenance dose is about 15.0 mg.

11. A method to improve weight management, in a patient in need thereof, comprising: administering an escalation dose about once weekly for a minimum of at least about two weeks and thereafter administering a maintenance dose about once weekly for a minimum of at least about two weeks; wherein the escalation dose is selected from the group consisting of about 2.5 mg, about 7.5 mg and about 12.5 mg of tirzepatide, or a pharmaceutically acceptable salt thereof; and wherein the maintenance dose is selected from the group consisting of about 5.0 mg, about 10.0 mg and about 15.0 mg of tirzepatide, or a pharmaceutically acceptable salt thereof.

12. The method of claim 11 to improve weight management, in a patient in need thereof, comprising: administering at least one escalation dose about once weekly for a minimum of about four weeks and at least one maintenance dose about once weekly for a minimum of about four weeks following the escalation dose; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg increment.

13. The method of claim 12, wherein the escalation dose is about 2.5 mg and the maintenance dose is about 5.0 mg.

14. The method of claim 12, wherein the escalation dose is about 7.5 mg and the maintenance dose is about 10.0 mg.

15. The method of claim 12, wherein the escalation dose is about 12.5 mg and the maintenance dose is about 15.0 mg.

16. A method for treating obesity, in a patient in need thereof, comprising: administering an escalation dose about once weekly for a minimum of at least about two weeks and thereafter administering a maintenance dose about once weekly for a minimum of at least about two weeks; wherein the escalation dose is selected from the group consisting of about 2.5 mg, about 7.5 mg and about 12.5 mg of tirzepatide, or a pharmaceutically acceptable salt thereof; and wherein the maintenance dose is selected from the group consisting of about 5.0 mg, about 10.0 mg and about 15.0 mg of tirzepatide, or a pharmaceutically acceptable salt thereof.

17. The method of claim 16 for treating obesity, in a patient in need thereof, comprising: administering at least one escalation dose about once weekly for a minimum of about four weeks and at least one maintenance dose about once weekly for a minimum of about four weeks following the escalation dose; wherein the escalation dose is selected from the group consisting of about 2.5 mg, about 7.5 mg and about 12.5 mg of tirzepatide, or a pharmaceutically acceptable salt thereof; wherein the maintenance dose is selected from the group consisting of about 5.0 mg, about 10.0 mg and about 15.0 mg of tirzepatide, or a pharmaceutically acceptable salt thereof; and wherein the maintenance dose following an escalation dose is a 2.5 mg increment.

18. The method of claim 17, wherein the escalation dose is about 2.5 mg and the maintenance dose is about 5.0 mg.

19. The method of claim 17, wherein the escalation dose is about 7.5 mg and the maintenance dose is about 10.0 mg.

20. The method of claim 17, wherein the escalation dose is about 12.5 mg and the maintenance dose is about 15.0 mg.

21. A method for improving glycemic control in a patient comprising administering to the patient tirzepatide in once weekly doses, the administering comprising:
administering a first once weekly dose of 2.5 mg for four weeks;
increasing the once weekly dose by increments of 2.5 mg to a once weekly maintenance dose of 5, 10 or 15 mg, where each increased once weekly dose is administered for at least four weeks; and
administering the maintenance dose of 5, 10, or 15 mg once weekly to improve the glycemic control in the patient.

22. The method of claim 21, wherein the patient has type 2 diabetes.

23. The method of claim 21, wherein the improved glycemic control comprises reducing the patient's level of HbA1c below 7%.

24. The method of claim 21, wherein the improved glycemic control comprises reducing the patient's level of HbA1c below 5.7%.

25. The method of claim 21, wherein the improved glycemic control reduces the patient's body weight by at least 5%.

26. The method of claim 21, wherein the improved glycemic control reduces the patient's body weight by at least 10%.

27. The method of claim 21, further comprising administering metformin to the patient.

28. The method of claim 21, wherein the maintenance dose is 5 mg.

29. The method of claim 21, wherein the maintenance dose is 10 mg.

30. The method of claim 21, wherein the maintenance dose is 15 mg.

31. The method of claim 30, further comprising reducing the maintenance dose to 10 mg.

32. The method of claim 21, wherein the administering the maintenance dose once weekly provides greater improved glycemic control and a reduced risk of nausea, vomiting, and diarrhea compared to treatment with 1.5 mg of dulaglutide once weekly.

33. The method of claim 21, wherein the administering the maintenance dose once weekly provides a less than a 31% of a risk experiencing a Previously Presented event of nausea, vomiting, and diarrhea on a weekly basis.

34. The method of claim 21, wherein the administering the maintenance dose once weekly provides not more than a 22% of a risk experiencing a Previously Presented event of nausea, vomiting, and diarrhea on a weekly basis.

35. The method of claim 21, wherein the tirzepatide is administered subcutaneously to the patient.

36. The method of claim 21, wherein the tirzepatide is administered as a 1 ml aqueous solution.

37. The method of claim 21, wherein the tirzepatide is administered as a pharmaceutically acceptable salt of tirzepatide.

38. The method of claim 22 wherein the tirzepatide is administered subcutaneously to the patient.

39. A method for improving glycemic control in a patient comprising administering to the patient tirzepatide in once-weekly doses, the administering comprising;
administering a first once-weekly dose of 2.5 mg for four weeks;
increasing the once-weekly dose by increments of 2.5 mg to a once weekly maintenance dose of 5, 10, or 15 mg, wherein each increased once weekly dose is administered for at least four weeks; and
administering the maintenance dose of 5, 10, or 15 mg once weekly to improve glycemic control in the patient, wherein the patient has type 2 diabetes and the tirzepatide is administered subcutaneously to the patient.

40. The method of claim 39, wherein the improved glycemic control comprises reducing the patient's level of HbA1c below 7%.

41. The method of claim 39, wherein the improved glycemic control comprises reducing the patient's level of HbA1c below 5.7%.

42. The method of claim 39, wherein the improved glycemic control reduces the patient's body weight by at least 5%.

43. The method of claim 39, wherein the improved glycemic control reduces the patient's body weight by at least 10%.

44. The method of claim 39, further comprising administering metformin to the patient.

45. The method of claim 39, wherein the maintenance dose is 5 mg.

46. The method of claim 39, wherein the maintenance dose is 10 mg.

47. The method of claim 39, wherein the maintenance dose is 15 mg.

48. The method of claim 47, further comprising reducing the maintenance dose to 10 mg.

49. The method of claim 39, wherein the administering the maintenance dose once weekly provides greater improved glycemic control and a reduced risk of nausea, vomiting, and diarrhea compared to treatment with 1.5 mg of dulaglutide once weekly.

50. The method of claim 39, wherein the administering the maintenance dose once weekly provides a less than a 31% of a risk experiencing a Previously Presented event selected from the group consisting of nausea, vomiting, and diarrhea, on a weekly basis.

51. The method of claim 39, wherein the administering the maintenance dose once weekly provides not more than a 22% of a risk experiencing a new event selected from the group consisting of nausea, vomiting, and diarrhea, on a weekly basis.

\* \* \* \* \*

UNITED STATES PATENT AND TRADEMARK OFFICE
CERTIFICATE OF CORRECTION

PATENT NO. : 12,343,382 B2
APPLICATION NO. : 17/366453
DATED : July 1, 2025
INVENTOR(S) : Charles T. Benson et al.

Page 1 of 1

It is certified that error appears in the above-identified patent and that said Letters Patent is hereby corrected as shown below:

In the Specification

Column 2; Line 32; Delete "tiral;" and insert -- trial; --.

In the Claims

Column 65; Line 34; Claim 21: Delete "where" and insert -- wherein --.

Column 66; Line 3; Claim 33: Delete "Previously Presented" and insert -- new --.

Column 66; Line 7; Claim 34: Delete "Previously Presented" and insert -- new --.

Column 66; Line 63; Claim 50: Delete "Previously Presented" and insert -- new --.

Signed and Sealed this
Twenty-fifth Day of November, 2025

John A. Squires
*Director of the United States Patent and Trademark Office*